United States Patent [19]

Akima et al.

[11] Patent Number: 5,733,891
[45] Date of Patent: Mar. 31, 1998

[54] COMPOUND FOR MEDICINAL INGREDIENT AND HYALURONIC ACID AND PROCESS FOR PRODUCING THE SAME

[75] Inventors: Kazuo Akima; Yuhei Iwata, both of Yokohama; Kayoko Matsuo, Hachiouji; Nobutoshi Watari, Kawasaki, all of Japan

[73] Assignee: Shiseido Co., Ltd., Tokyo, Japan

[21] Appl. No.: 380,324

[22] Filed: Jan. 30, 1995

Related U.S. Application Data

[63] Continuation of Ser. No. 861,852, filed as PCT/JP91/01431, Oct. 18, 1991 published as WO92/06714, Apr. 30, 1992, abandoned.

[30] Foreign Application Priority Data

Oct. 18, 1990 [JP] Japan .................................. 2-280628
Jun. 3, 1991 [JP] Japan .................................. 3-159611

[51] Int. Cl.$^6$ .......................... A61K 31/70; C07H 1/00; C07H 15/00
[52] U.S. Cl. ............................. 514/59; 514/34; 536/6.4; 536/18.5; 536/55.1
[58] Field of Search ........................... 536/6.4, 55.1, 536/18.5; 514/54, 34

[56] References Cited

FOREIGN PATENT DOCUMENTS

| 0416250 | 3/1991 | European Pat. Off. |
|---|---|---|
| 54-14513 | 2/1979 | Japan . |
| 61-229816 | 10/1986 | Japan . |
| 62-64802 | 3/1987 | Japan . |
| 62-255428 | 11/1987 | Japan . |
| 63-253030 | 10/1988 | Japan . |
| 63-264427 | 11/1988 | Japan . |
| 154002 | 3/1989 | Japan . |
| 2231078 | 9/1990 | Japan . |
| 1287041 | 11/1990 | Japan . |
| WO 9005522 | 5/1990 | WIPO . |
| WO 9104058 | 4/1991 | WIPO . |

OTHER PUBLICATIONS

Migrdichian, Organic Synthesis, vol. 1, (195) p. 49–50.
Chemical Abstracts; vol. 114, No. 5, 1990, Abstract No. 35520U , Ouchi, et al., "Design of Polysaccharide–5–Flourouracil Conjugates Exhibiting . . . ".

Chemical Abstracts; vol. 108, No. 24, 1988, Abstracts No. 210111m, Cera et. al., "Anthracycline Antibiotics Supported on Water–Soluble Polysaccharides".

Journal of Cell Science;"CD44: The Hyaluronan Receptor: pp. 293–298; 1992; Charles Underhill.

Advanceds Drug Delivery Review; "Clearence of Hyaluronan From the Circulation" pp. 221–241; 1991; Lena Lebel.

Cell; vol. 65; pp. 13–24; 1991; "A New Variant Of Glycoprotein CD44 Confers Metastatic Potential To Rat Carcinoma Cells; U. Gunthert, et al.

The Journal Of Cell Biology; vol. 116, No 4, pp. 1055–1062; 2.92; "The Hyaluronan Receptor (CD44) Participates In The Uptake And . . . ; M. Cully, et al.

International Journal of Macromol.; 198, vol. 10.; pp. 66–74; "Anthracycline Antibiotics Supported On Water–Soluble Polysaccharides: Synthesis And Physicochemical Characterization"; C. Cera, et al.

International Symposium; Delivery of Protein Drugs–The Next 10 Years; Sep. 2, 1993; K. Akima et al; "Evaluation of Antitumor Activities of Hyaluronate Binding Antitumor Drug–Synthesis, Characterization and Antitumor Activities".

84th Annual Mtg., American Association Of Cancer Research; Mar. 1993; vol. 34; pp. 33–36, 61, 68, 71, 91, and 93.

Cancer Research; vol. 54, pp. 422–426, Jan. 15, 1994; "Potential Use Of Soluble CD44 In Serum As Indicator Of Tumor Burden and Metastasis In Patient With Gastic or Colon Cancer; Y. Guo, et al.

Cancer Cells, Sep. 1991, vol. 3, No. 9, pp. 347–350; "The Transmembrane Hyaluronate Receptor (CD44) :Multiple Functions, Multiple Forms; B. Haynes, et al.

*Primary Examiner*—Elli Peselev
*Attorney, Agent, or Firm*—Townsend & Banta

[57] ABSTRACT

A compound of hyaluronic acid and a medicinal ingredient produced by the convalent bonding (preferably amide bonding) of hyaluronic acid and the medicinal ingredient, and a process for preparing the same.

The hyaluronic acid portion is completely decomposed by metabolism in the action region, whereby the medicinal ingredient is gradually and quantitatively released.

21 Claims, 17 Drawing Sheets

HYALURONIC ACID

— MITOMYCIN C
— E D C I
— N-HYDROXYSUCCINIMIDE

OR

COMPOUND FOR MEDICINAL INGREDIENT AND HYALURONIC ACID AND PROCESS FOR PRODUCING THE SAME

This application is a continuation of application Ser. No. 07/861,852, filed as PCT/JP91/01431, Oct. 18, 1991 published as WO92/06714, Apr. 30, 1992, now abandoned.

[TECHNICAL FIELD]

The present invention relates to a compound of hyaluronic acid and a medicinal ingredient and a process for producing the same and, more particularly, to a compound of hyaluronic acid and a medicinal ingredient which utilizes the directivity of hyaluronic acid to a specific part in the living body and a process for producing the same.

[BACKGROUND ART]

It is very important for a medicinal ingredient such as an anticancer agent to exert the desired medicinal action on the desired part in the living body free from harmful side effects on living body.

In order to reduce the harmful side effects of a medicinal ingredient, it is desirable to use a medicinal ingredient which has few harmful side effects itself. However, if it is possible to direct a medicinal ingredient only to the action region, the harmful side effects on the other tissues are greatly reduced.

On the basis of this principle, development of what is called a drug delivery system is in progress. This technique has become inevitable to the administration of a medicine which has generally strong side effects such as an anticancer agent.

A general drug delivery system in living body, however, fundamentally depends upon or is influenced by the systemic circulation blood, so that it is very difficult to exclude the systemic influence of a medicine.

Therefore, an appropriate administration of a medicine which has harmful side effects on other tissues in spite of having a striking medicinal effect is very difficult.

Since conventional medicinal ingredients have a low directivity to a specific diseased part, especially, cancer tissues and the like, it is necessary to administrate a large amount of medicinal ingredient in order to produce adequate medicinal effects.

To solve this problem, an example is known of reducing the harmful side effects of a medicine and improving the medicinal effects by combining a medicinal ingredient with various high-molecular substances such as dextrane and albumin and utilizing the directivity of the high-molecular substances and the gradual releasability of the medicinal ingredient.

Few of the high-molecular substance conventionally used, however, are derived from the human body. When those substances are applied to the human body, the burden imposed on the human body at the time of decomposition by metabolism of the substance is heavy.

Even in the case of using dextrane, the structure of the high-molecular substance is changed into a substance which does not exist in the human body at the time of condensation reaction.

[DISCLOSURE OF INVENTION]

Accordingly, it is an object of the present invention to eliminate the above-described problems in the prior art and to provide a compound of hyaluronic acid and a medicinal ingredient which is capable of exhibiting efficient medicinal effects while suppressing the influence on the other tissues as much as possible.

As a result of studies undertaken by the present inventors so as to attain this aim, it has been found that the compound of hyaluronic acid and a medicinal ingredient having a high directivity to a specific part in the living body is obtained by combining the medicinal ingredient with hyaluronic acid which constantly exists in the living body. The present invention has been achieved on the basis of this finding.

In a first aspect of the present invention, there is provided a compound of hyaluronic acid and a medicinal ingredient produced by combining hyaluronic acid and the medicinal ingredient by convalent bonding.

In a second aspect of the present invention, there is provided a compound of a hyaluronic acid and a medicinal ingredient produced by combining the medicinal ingredient with the carboxyl group of the glucuronic acid residue of the hyaluronic acid by amide bonding.

In a third aspect of the present invention, there is provided a suppressor for a cancer metastasis through lymph nodes which is produced by combining hyaluronic acid with an anticancer agent as a medicinal ingredient.

In a fourth aspect of the present invention, there is provided a non-specific missile therapeutic agent for cancer which is produced by combining hyaluronic acid with an anticancer agent as a medicinal ingredient.

In a fifth aspect of the present invention, there is provided a suppressor for a cancer metastasis through lymph nodes which is produced by combinig acetylated hyaluronic acid with a medicinal ingredient.

In a sixth aspect of the present invention, there is provided a non-specific missile therapeutic agent for cancer which is produced by combining acetylated hyaluronic acid with a medicinal ingredient.

In a seventh aspect of the present invention, there is provided a process for preparing a compound of hyaluronic acid and a medicinal ingredient comprising the steps of: adding pyridine and hydrochloric acid to an aqueous solution of sodium hyaluronate; stirring the mixture; adding 1-ethyl-3-(3-dimethylaminopropyl)carbodiimide (EDC) and N-hydroxysuccinimide to the mixture so as to activate the hyaluronic acid ;dissolving the activated hyaluronic acid in a phosphoric acid buffer solution; and adding an aqueous solution of a medicinal ingredient to the resultant solution so as to combine the activated hyaluronic acid with the medicinal ingredient.

In an eighth aspect of the present invention, there is provided a process for preparing a compound of hyaluronic acid and a medicinal ingredient comprising the step of reacting acetylated hyaluronic acid with a medicinal ingredient in an organic solvent by a synthesis process which is impossible in an aqueous solution.

In a ninth aspect of the present invention, there is provided a process for preparing a compound of hyaluronic acid and a medicinal ingredient comprising the steps of: reacting acetylated hyaluronic acid with a medicinal ingredient in an organic solvent; and removing the acetyl group from the reaction product.

Example of a medicinal ingredient used in the present invention are: antibiotic antitumor agents such as mitomycin C, daunomycin, chromomycin A3, bleomycin, neocarzinostatin, actinomycin D, adriamycin and mithramycin;

alkylated antitumor agents such as his (2-chloroethyl)-amine(nitrogen mustard) derivative, aziridine derivative, methansulfonic acid ester derivative, N-alkyl-N-nitrosourea derivative, alkyl bromide derivative, mechlorethamine hydrochloride, chloraOmbutyl, melphalan, cyclophosphamide, triethylenemelamine, thiotepa and busulfan;

anti-metabolical anititumor agents such as mercaptopurine, fluorouracyl, N1-(2-tetrahydrofuryl)-5-fluorouracyl and ancitabine hydrochloride;

hormonnal antitumor agents such as diethylstilbestrol, hexestol, ethynylestradiol, testosterone propionate, fluoxymesterone, dolomostannorone propynate, predonisone and predonisolone;

L-asparaginase; and vinca alkaloids.

All of the kinetics of hyaluronic acid in the body and all of the kinetics of a compound of hyaluronic acid and a medicinal ingredient have not been clarified yet.

The present inventors investigated the kinetics of hyaluronic acid in the body by using $^{14}$C-labelled sodium hyaluronate having a molecular weight of 1,000 kd.

The $^{14}$C-labelled hyaluronic acid was administered to a knee joint cavity and the subcutis of a femoral region of a male SD rat (weight: 350 to 500 g). It is because the regional lymph nodes of the knee joint cavity and the femoral region are evident that these regions are selected as the parts to which the $^{14}$C-Labelled hyaluronic acid was administered.

The tissues collected in the case of administering the hyaluronic acid to the knee joint cavity were lumbar lymph nodes which are the regional lymph nodes and the mesenteric lymph nodes which are not regional lymph nodes, the liver and the spleen, which are the main metabolic tissues in the case of intravenous administration, all blood and plasma.

In the case of administering the hyaluronic acid to the subcutis of the femoral region, the angina lymph nodes which are the other regional lymph nodes of the femoral region was added to the above-described tissues.

The tissue collecting times in the case of administering the hyaluronic acid to the knee joint cavity were 3, 6, 24 and 96 hours after the administration. The tissue collecting time in the case of administering the hyaluronic acid to the subcutis of the femoral region was 6 hours after the administration. In the case of administering the hyaluronic acid to the knee joint cavity, the concentration of hyaluronic acid was also measured in the iliac lymph nodes and in the liver 6 and 24 hours after the administration.

FIGS. 1 to 4 show the distribution of hyaluronic acid in the respective tissues observed 3, 6, 24 and 96 hours, respectively, after the administration of the hyaluronic acid to the knee joint cavity, and FIG. 5 shows the distribution of hyaluronic acid in the respective tissues observed 6 hours after the administration of the hyaluronic acid to the subcutis of the femoral region.

As is clear from these graphs, a high directivity to the regional lymph nodes of the region to which the hyaluronic acid had been administered was observed irrespective of the time elapsed after the administration. Especially, when the iliac lymph nodes, which are the regional lymph nodes of the knee joint cavity, were observed 3 hours after the administration, the radioactivity concentration in the regional lymph nodes was not less than 200 times that in the plasma and not less than 50 times that in the liver. That is, the directivity of the hyaluronic acid to the regional lymph nodes was remarkably high. The radio activity concentration in the regional lymph nodes 96 hours after the administration was also maintained at a high value. Thus, the persistence of the hyaluronic acid was also suggested.

When the concentration of hyaluronic acid in the regional lymph tissues and in the liver 6 hours after the administration was measured, it exhibited a high value in the lymph nodes but no hyaluronic acid was detected in the liver. These results suggest that although the radioactivity distribution in the regional lymph nodes shows the distribution of the hyaluronic acid, the radioactivity distribution in the liver shows the distribution of the metabolite of the hyaluronic acid.

From these investigation, it has been found that hyaluronic acid specifically moves to the regional lymph nodes of the region to which the hyaluronic acid is administered and is decomposed by metabolism in the lymph nodes.

It has also been found that when sodium hyaluronate is administered to the body, it specifically concentrates at tumor tissue.

The present inventors took notice of the properties of high-molecular weight hyaluronic acid as an excellent carrier and undertook various studies on the combination of high-molecular weight hyaluronic acid with a medicinal ingredient and have finally succeeded in the synthesis of a compound of hyaluronic acid and a medicinal ingredient which maintain the physicochemical properties of hyaluronic acid.

When a compound according to the present invention is administered, for example, to a subcutaneous tissue and a muscular tissue in the vicinity of cancer of a patient, the compound specifically moves to the regional lymph nodes of the region in which the cancer grows and is maintained in the lymph nodes. In addition, the anticancer agent is quantitatively released due to the decomposition of the hyaluronic acid by metabolism in the lymph nodes. The compound exhibits almost no harmful side effects due to the excellent directivity to the lymph nodes and almost completely suppresses the metastasis of the cancer through lymph nodes.

Furthermore, since hyaluronic acid specifically gathers to a diseased tissue, especially, a tumor tissue, it is possible to concentrate a medicinal ingredient onto the action region at a high concentration so as to efficiently produce the medicinal effect even with the administration of a small does of a compound of hyaluronic acid and a medicinal ingredient.

[BEST MODE FOR CARRYING OUT THE INVENTION]

The preferred embodiments of the present invention will be described in detail with reference to the accompanying drawings.

A compound of hyaluronic acid and an anticancer agent can be prepared in the following manner as an example of a compound of hyaluronic acid and a medicinal ingredient.

As the raw materials, high-molecular sodium hyaluronate [prepared from the supernatant of cultured streptococcus zooepidemicus: Akasaka et al, *Nihon Keshohin Gijutsusha Kaishi*(The Journal of The Society of Cosmetics Technicians of Japan )22, 35–42, 1988] and commercially available mitomycin C (produced by, e.g., Sigma) are usable.

A high-molecuar agent and a low-molecular agent are generally combined by cyan bromide method, periodic acid oxidization method, epichlorohydrin method, mixed acid anhydride method, carbodiimide method, active ester method, glutaraldehyde method and SPDP(N-Succinimidyl 3-(2-pyridyldithio)propionate) method, or the like.

Among these, it is preferable that a medicinal ingredient is combined with the carboxyl group of the glucuronic acid residue of the hyaluronic acid by amide bonding. Particularly, by using a water-soluble carbodiimide reagent (e.g., 1-ethyl-3-(3-dimethyl-aminopropyl) carbodiimide (EDC), and 1-cylcohexyl-3-(2-morphorinyl-(4)-ethyl)-carbodiimide-methyl-p-toluene sulphonate), it is possible to obtain a medicinal ingredient combined with the glucuronic acid residue by amide bonding without influencing the fundamental structure of hyaluronic acid.

The present invention will be explained in more detail with reference to the following examples.

EXAMPLE 1

Compound of Hyaluronic Acid and Mitomycin C
Production Example 1

Hyaluronic acid itself is an ingredient of the living body, so that it involves no fear of antigenicity, as described above. In addition, since hyaluronic acid is gradually decomposed in the action region in the body, it is expected to graually and quantitatively release the medicinal ingredient with the decomposition.

In a conventional method of combining a high-molecular substance and a medicinal ingredient, however, the fundamental structure of hyaluronic acid changes at the time of reaction, so that it is difficult to obtain the expected nonantigenicity and gradual releasability of a medicinal ingredient.

The present inventors investigated the amide bonding between hyaluronic acid and a medicinal ingredient which utilizes the glucuronic acid residue of hyaluronic acid so as not to change the fundamental structure of hyaluronic acid.

Since hyaluronic acid is difficult to dissolve in an organic solvent, it is impossible to bring hyaluronic acid into reaction except in the form of an aqueous solution. On the other hand, since an amide reaction is a dehydration reaction, it is generally carried out in an anhydrous system.

Figure 1:
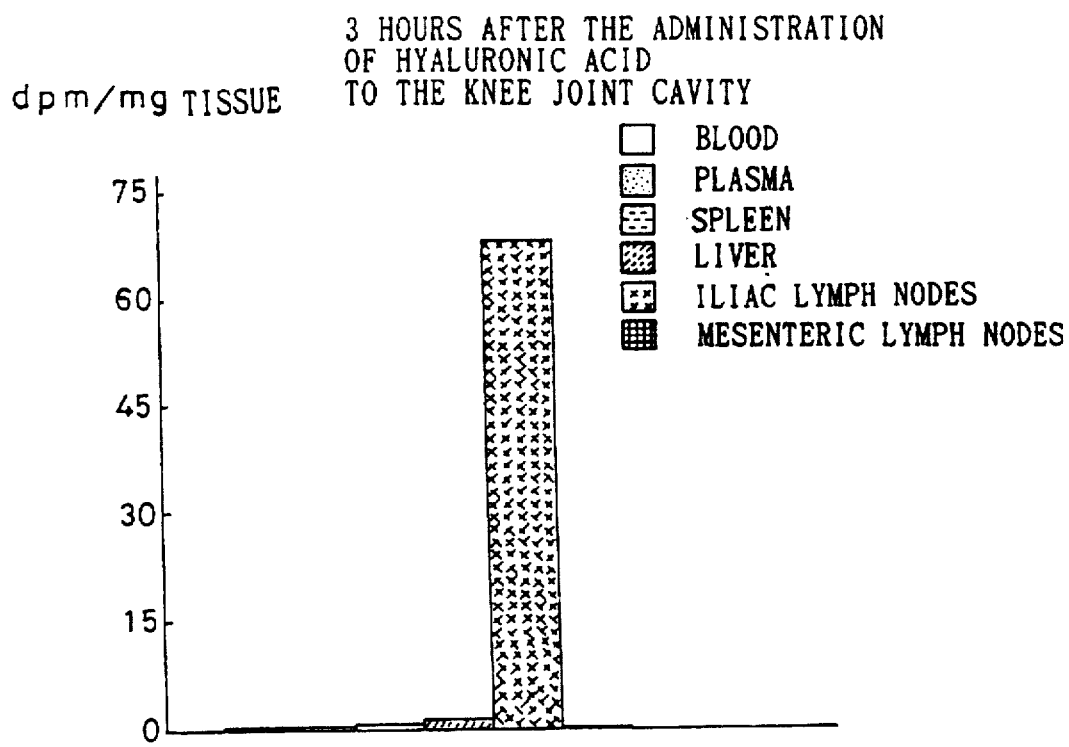
FIGS. 1 to 4 are explanatory views of the distribution of $^{14}$C in each tissue after a predetermined time passed since the administration of $^{14}$C-labelled hyaluronic acid to a knee joint cavity of rats.
Figure 2:
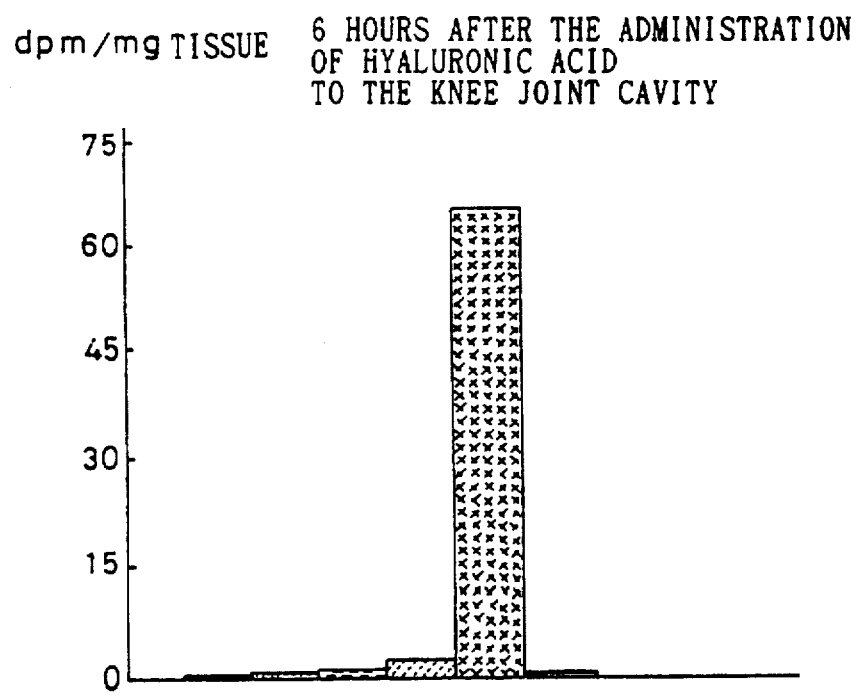
Figure 3:
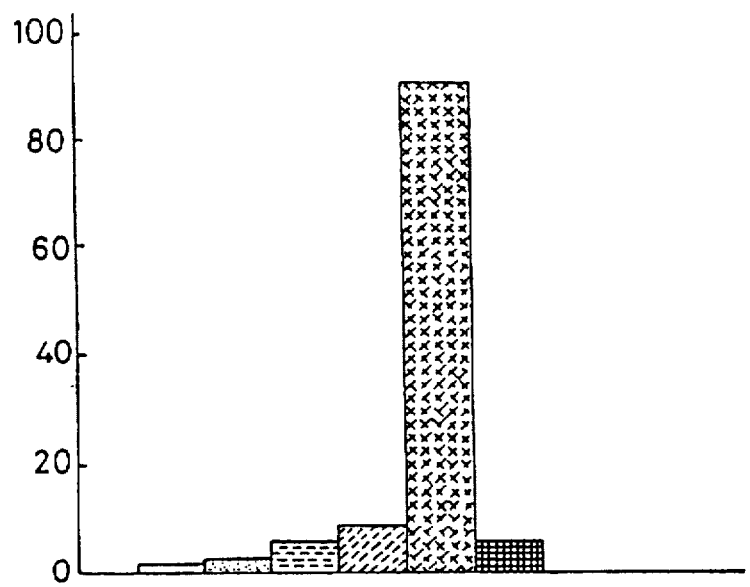
Figure 4:
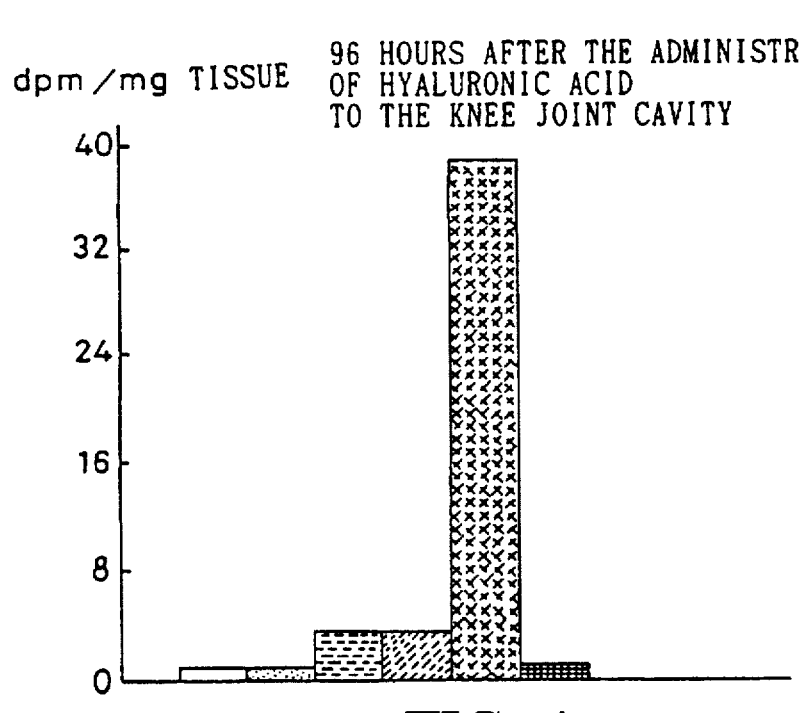
Figure 5:
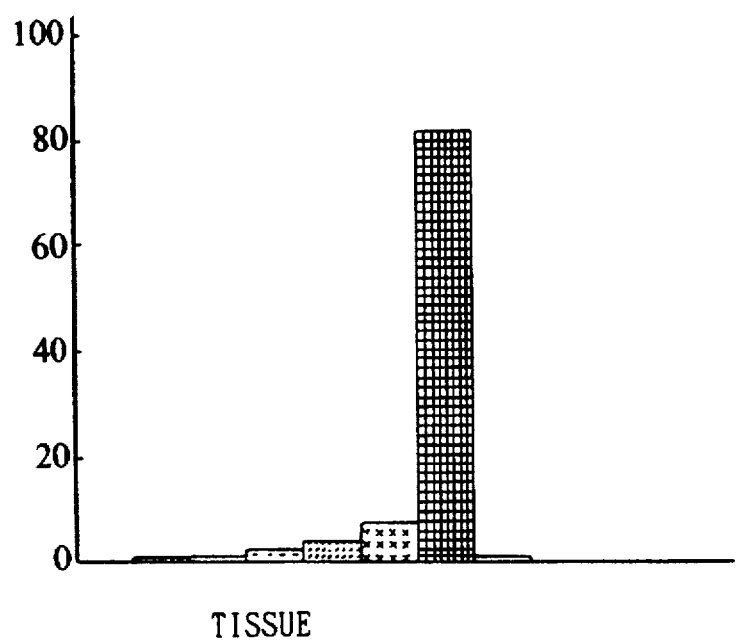
FIG. 5 is an explanatory view of the distribution of $^{14}$C in each tissue after 6 hours passed since the administration of $^{14}$C-labelled hyaluronic acid to the subcutis of a femoral region of rats.
Figure 6:
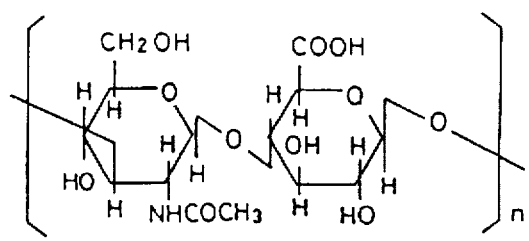
FIG. 6 is an explanatory view of the process for preparing a compound of hyaluronic acid and mitomycin c.
Figure 6:
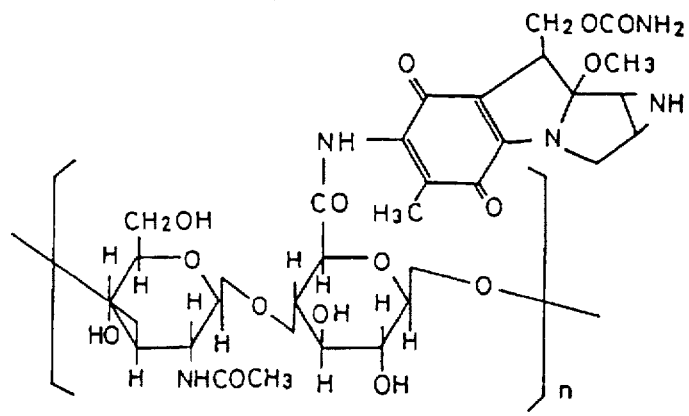
Figure 6:
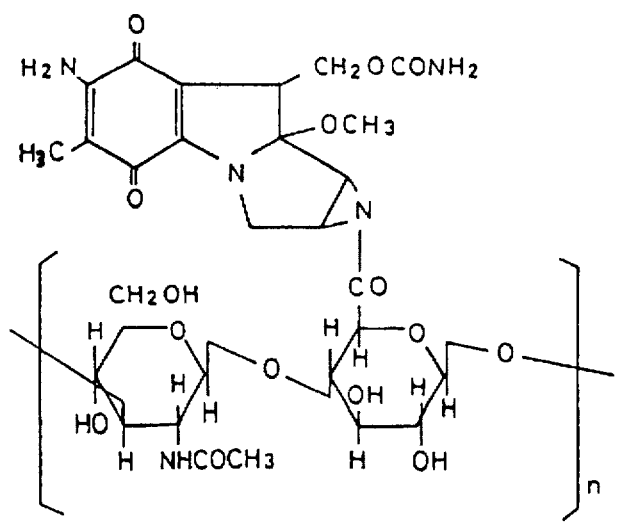

The present inventors carried out an amide reaction, which is a dehydration reaction, in a water system by the following process(see FIG. 6), thereby enabling amide bonding of a comparatively large amount of medicinal ingredient with hyaluronic acid without changing the fundamental structure of hyaluronic acid.

The reaction of a compound of hyaluronic acid and a medicinal ingredient inside and outside the body is similar to that of hyaluronic acid in the single form.

400 μl of pyridine and 2 ml of 2N hydrochloric acid were added to 10 ml of an aqueous solution of 1% sodium hyaluronate. After the mixture was thoroughly stirred, 1 ml of 1M EDC and 1 ml of 1M N-hydroxysuccinimide were added thereto and the resultant mixture was thoroughly stirred so as to be uniform. The mixture was reacted for 5 hours at room temperature.

2 ml of a 1M sodium acetate butter solution (pH:6.0) was then added and the reaction was continued for further 30 minutes, thereby decomposing the surplus carbodiimide.

Acetone was then added to the reaction product under stirring so that the final concentration was 60% (w/v). The precipitate of the solution was gathered by the centrifugation of the solution at 3000 rpm for 30 minutes, and the gathered precipitate was dissolved again in 2% sodium acetate so that the concentration was about 1% .The precipitate was gathered again in the same method by adding acetone. By repeating this acetone precipitating process three times, activated N-hydroxysuccinimidehyaluronic acid was obtained.

The activated hyaluronic acid obtained was dissolved in 10 ml of a 0.1M phosphoric acid buffer solution (pH:7.2)

and 2 ml of an aqueous solution of 1% mitomycin C was added to the solution. The solution was reacted for 2 days at room temperature. At the end of the reaction, triple the amount of acetone relative to the whole amount of solution was added and centrifuged so as to obtain the precipitant of the reaction product. By repeating this acetone precipitating process three times, a pure compound of hyaluronic acid and mitomycin C was obtained. The final precipitate was dried at room temperature by a vacuum drier to obtain a dark purplish red powder.

In this way, according to this process, an amide reaction, which is a dehydration reaction, can be carried out in an aqueous solution.

The amount of aqueous solution of 1% mitomycin C added to the solution of the activated hyaluronic acid is in the range of 0.1 to 5 ml, and the color of the powder finally obtained is light purplish red to dark purplish red in accordance with the concentration of mitomycin C.

Figure 7:
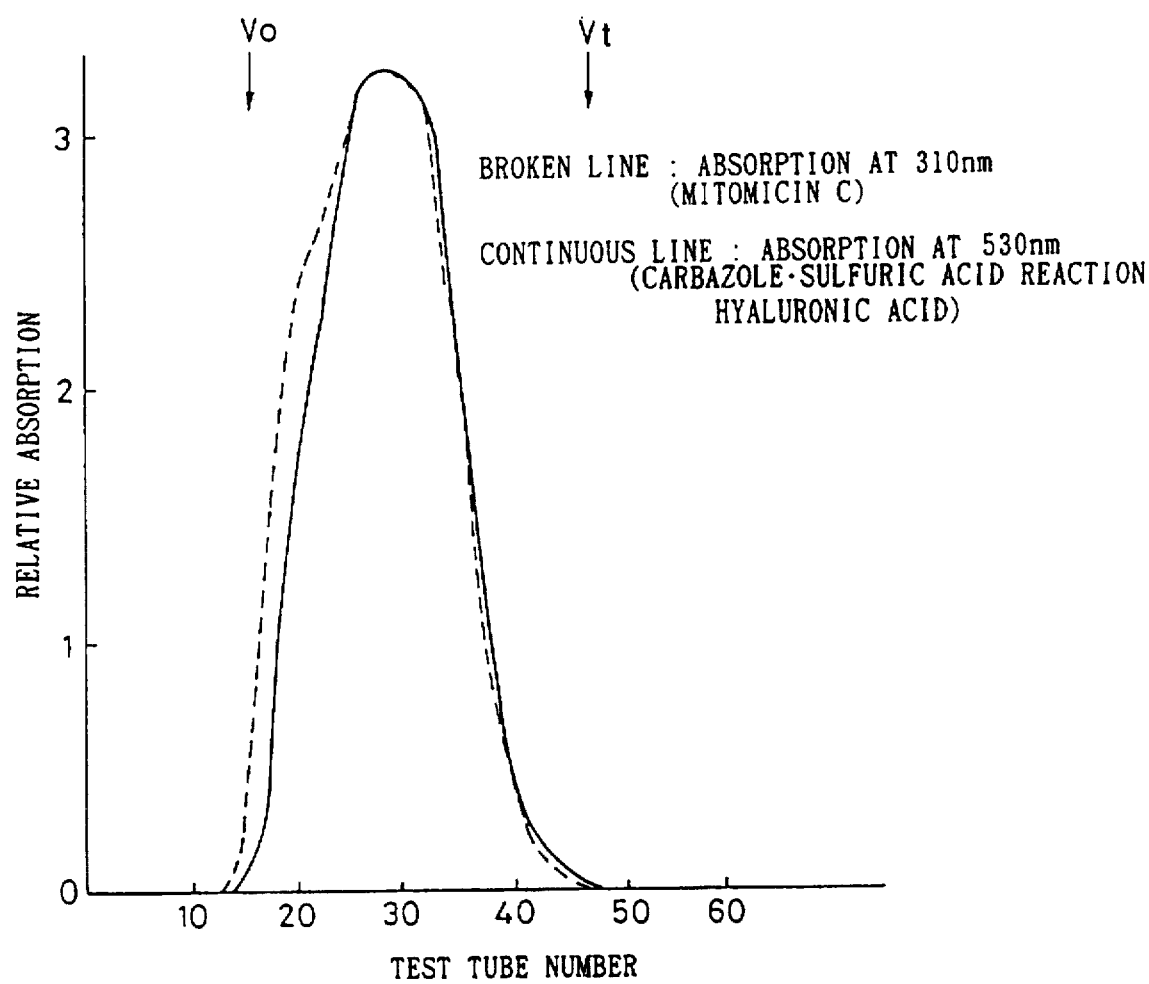
FIG. 7 is an explanatory view of the gel permeation pattern of a compound of hyaluronic acid and a medicinal ingredient according to the present invention.

The powder obtained was dissolved in an isotonic phosphat buffered saline buffer solution to a concentration of 0.5% (w/v) and filtered out through a membrane filter of 0.22 μ to obtain an axenic injectant. When the solution was diluted to 10 times by the isotonic phosphoric acid buffer solution, added to a gel permeation column of Sephacryl S-1000 and detected by the carbazole.sulfuric acid reaction and the absorption of the ultraviolet portion, the absorption of the ultraviolet portion derived from mitomycin C was detected at 310 nm, which agreed with the elution position of hyaluronic acid (see FIG. 7).

The compound of hyaluronic acid and mitomycin C obtained has the following nature.

(1) Molecular weight: 10 to 10,000 kd (calculated by Sephacryl S-1000 chromatography calibrated by hyaluronic acid having various molecular weights or an intrinsic viscosity method)

(2) Content of anticancer agent (mitomycin C): 0.1 to 30 wt % (this content can be varied by varying the amount of carbodiimide as a carboxyl group activator and the amount of anticancer used for the reaction)

(3) Nature: Light purplish red to dark purplish red color in an aqueous solution of 0.5% (w/v) of the compound.

(4) Solubility: Soluble to water, physiological saline solution and an isotonic phosphoric acid buffer solution and insoluble to methanol, acetone, ether and chloroform.

(5) Color reaction: Positive to a carbazole.sulfuric acid reaction, and an Elson-Morgan reaction after hydrolysis with acid.

(6) Ultraviolet portion absorption: The peaks of the spectrum are at 252 nm and 310 nm, and the shoulder thereof is in the vicinity of 360 nm.

(7) Release of anticancer agent: Mitomycin C is released in the living body with the decomposition of hyaluronic acid. The amido bond is hydrolized by treating the compound with a strong alkali and mitomycin C is released.

(8) Gel permeation pattern: When the compound is added to a gel permeation column of Sephacryl S-1000 and thereafter subjected to a carbazole.sulfuric acid reaction, the peak of the compound is observed at the position of a molecular weight of 500 kd. At the same position, the absorption of the ultraviolet portion derived from mitomycin C is observed (see FIG. 7).

Figure 8:
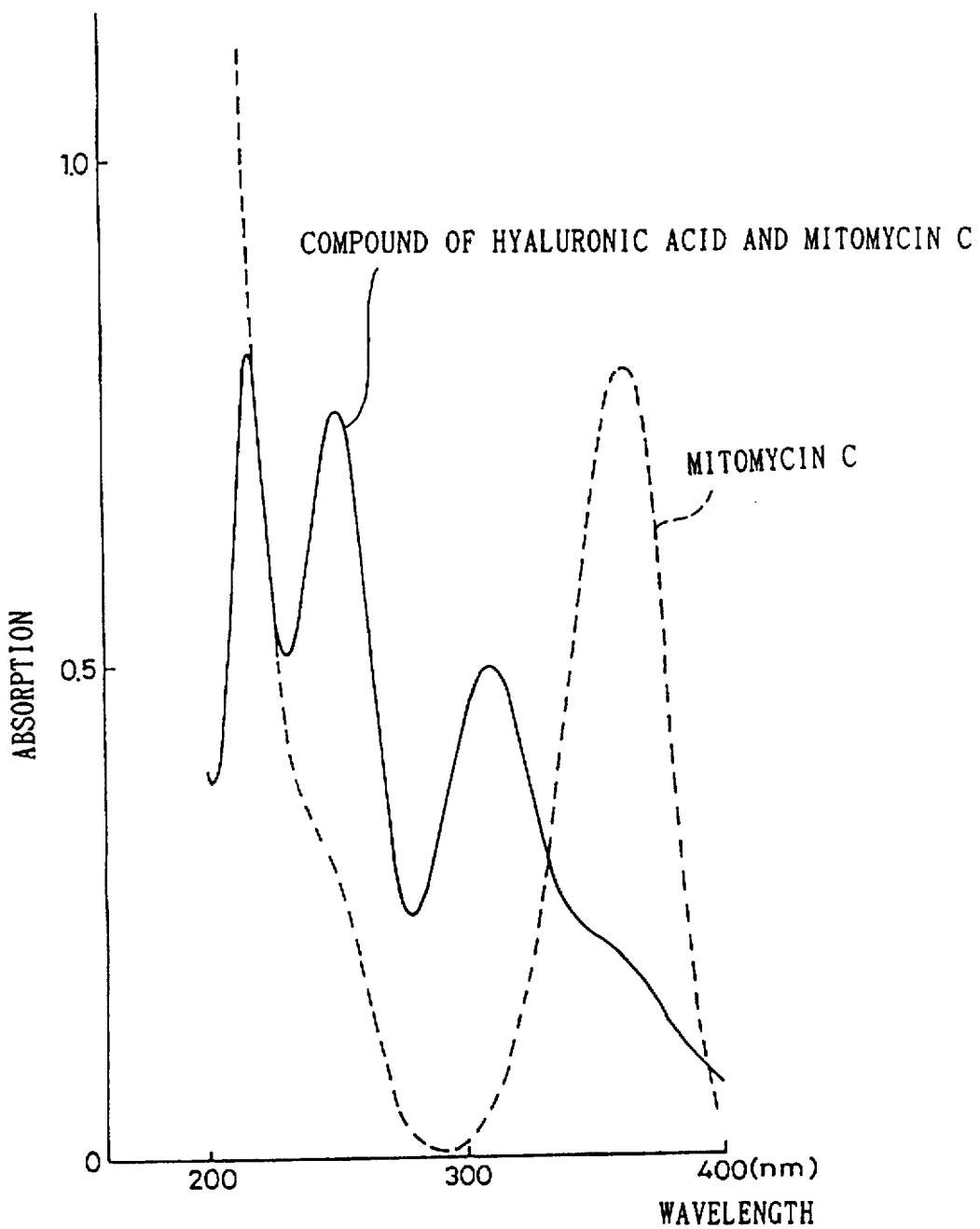
FIG. 8 is an explanatory view of the ultraviolet portion absorption spectra of sodium hyaluronate and a compound of hyaluronic acid and a medicinal ingredient according to the present invention.

When sodium hyaluronate was dissolved in water, no ultraviolet portion absorption was observed at not less than 230 nm, but in the compound of hyaluronic acid and mitomycin C of the present invention, the peaks were at 252 nm and 310 nm, and the shoulder thereof was in the vicinity of 360 nm (see FIG. 8).

Figure 9:
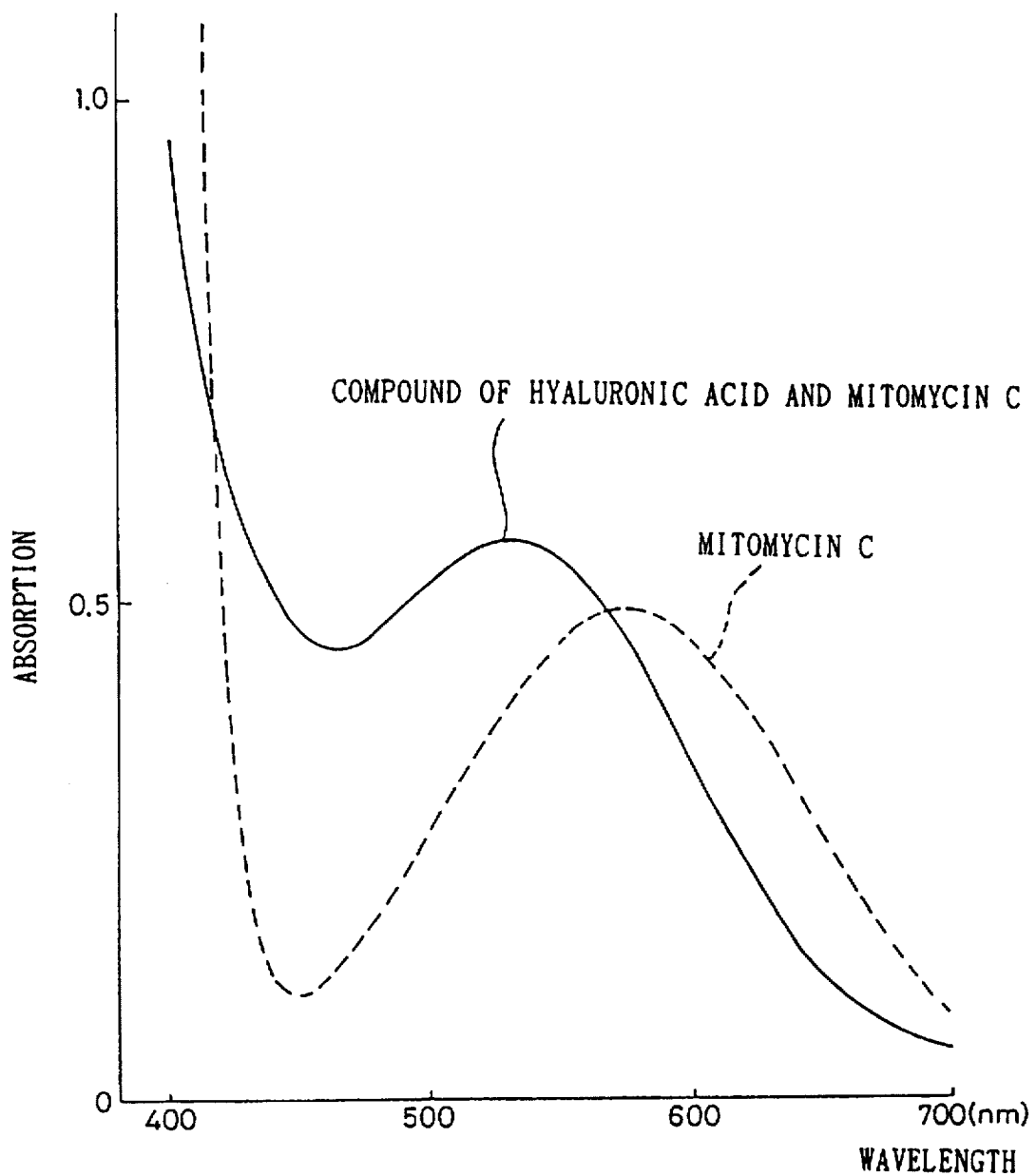
FIG. 9 is an explanatory view of the visible portion absorption spectra of sodium hyaluronate and a compound of hyaluronic acid and a medicinal ingredient according to the present invention.

The visible portion absorption was observed in a broad area with 528 nm as the center (see FIG. 9).

Under an acidic condition of 0.1N, the ultraviolet portion absorption was observed in the vicinity of 245 nm both in the free mitomycin C and the compound. In the case of the free mitomycin C, a new absorption was observed at 308 nm which is based on the stabilization of the aromatic ring of an amino group under an acidic condition. The absorbing wavelength approximately agreed with that of the compound.

In this example, the mitomycin C content (wt %) calculated from the absorbances of the free mitomycin C and the compound in the vicinity of 245 nm was 11.5% and about ⅙ of the free carboxyl groups were substituted by mitomycin C.

Sodium hyaluronate used as the carrier in the present invention is originally an ingredient of the living body which exists in large amount in connective tissues and the like. After sodium hyaluronate is completely decomposed in lymph nodes, it is reused mainly as a carbon source. The safety of sodium hyaluronate is therefore much higher than that of a conventional high -molecular carrier.

In addition, since the compound of hyaluronic acid and an anticancer agent has a high directivity to lymph nodes, the concentration of the anticancer except in lymph nodes is not more than several-% of the concentration of the anticancer in the case at single administration. It is therefore possible to safely apply the compound to a patient suffering from cancer at a very early stage, or even to a patient whose disease is not yet definitely diagnosed as cancer, for the purpose of prevention.

In addition, due to the directivity of hyaluronic acid to a cancer tissue, it is possible to efficiently produce a medicinal effect on the diseased tissue while suppressing the concentration of mitomycin C in the body to a low value.

Production Example 2

2 ml of pyridine and 10 ml of 2N hydrochloric acid were added to 120 ml of an aqueous solution of 0.5% sodium hyaluronate in that order to adjust the pH to 4.75. Thereafter, 2 g of 1-ethyl-3-(3-dimethylaminopropyl) carbodiimide (EDC) and 1.5 g of N-hydroxysuccinimide were added thereto and the mixture was reacted for 5 hours at room temperature so as to activate the carboxyl group of hyaluronic acid. After decomposing the surplus EDC by adding a 1M sodium acetate solution, activated sodium hyaluronate was purified by repeating an acetone precipitating process three times. The activated hyaluronic acid obtained was dissolved in 120 ml of a 0.1M phosphoric acid buffer solution and 300 mg of mitomycin C was added to the solution. The solution was reacted for 2 days at room temperature. The reaction product was purified by repeating an acetone precipitating process three times in the same way, thereby obtaining about 600 mg of a pure compound of hyaluronic acid and mitomycin C.

The molecular weight of the compound of hyaluronic acid and mitomycin C calculated from the intrinsic viscosity thereof was 227 kd and the mitomycin C content was 3.5% (w/w).

Cancer Metastasis Suppressing Effect Test (1)

The cancer metastasis suppressing effect test applied to a compound of hyaluronic acid and mitomycin C according to the present invention will now be explained.

The compound in the Production Example 2 was dissolved in a physiological saline solution for injectants to a concentration of 4% (w/v). The cancer metastasis suppressing effect of the administration of the compound was compared with that of the administration of mitomycin C in the single from while administering the physiological saline solution to a controlled group.

A female C57BL/6 mouse (6 weeks old) was innoculated with 1×10⁵ of Lewis lung carcinoma cells on the subcutis of a flank region. Each group consisted of 6 mice. Each of the compound and mitomycin C was administered to the subcutis of the flank region of each mouse on the other side of the cancer-cells-innoculated region in three levels of 0.5, 1.0 and 5.0 mg/kg as calculated in terms of mitomycin C.

On the first day after the innoculation of the cancer cells, the corresponding medicine was administered for the first time. The second and third administrations were on the third and fifth days, respectively, after the innoculation. Each mouse having the cancer cells was killed 22 days after the innoculation and the weight of the cancer cells which had metastasized to the lung was measured. The antitumor effect was evaluated from the tumor growth suppression ratio represented by the following formula:

Tumor growth suppression ration=100×[(the weight of the cancer cells which had metastasized to the lung of the controlled group-the weight of the cancer cells which had metastasized to the lung of the group to which the corresponding medicine was administered)]/(the weight of the cancer cells which had metastasized to the lung of the controlled group) The results are shown in Table 1.

TABLE 1

| Medicine | Dose (mg/kg) × number of times | Suppression ration (%) |
| --- | --- | --- |
| Controlled group | | 0.0 |
| compound of hyaluronic acid and mitomycin | 1.0 × 1 | 64.6 |
| | 5.0 × 1 | 57.4 |
| Mitomycin C | 1.0 × 1 | −14.9 |
| | 5.0 × 1 | 83.4 |
| Compound of hyaluronic acid and mitomycin C | 0.5 × 3 | 99.4 |
| | 1.0 3 | 63.5 |
| Mitomycin C | 0.5 × 3 | 51.1 |
| | 1.0 × 3 | 30.5 |

As is clear from Table 1, the compound of hyaluronic acid and mitomycin C according to the present invention produced excellent cancer metastasis suppressing effect both in a single administration and in consecutive administrations than mitomycin C in the single form. Especially, the compound produced a striking effect in the three consecutive administration.

Cancer Metastasis Suppressing Effect Test (2)

The effect of a compound of hyaluronic acid and mitomycin C on the suppression of cancer metastasis through lymph nodes will now be explained.

The compared obtained in the Production Example 2 was dissolved in a physiological saline solution for injectants to a concentration of 4% (w/v). The cancer metastasis suppressing effect of the administration of the compound was compared with that of the administration mitomycin C in the single form while administering the physiological saline solution to a controlled group.

1×10⁶ of MH-134 ascites hepatoma cells were transplanted on the subcutis of a foot-pat of a female C3H/He mouse. Each group consisted of 6 mice. Each of the compound and mitomycin C was administered to the subcutis of the femoral region of each mouse on the same side of the cancer-cells -transplanted region in two levels of 0.1 and 1 mg/kg as calculated in terms of mitomycin C. On the days after the transplantation of the cancer cells, the corresponding medicine was administered for the first time and thereafter it was administered three times a week. Each mouse having the cancer cells was killed 21 days after the transplantation, and the minor diameter (nm) and the major diameter(nm) of an inguinae lymph node was measured. The tumor diameter was expressed by the product of the minor diameter and the major diameter. The enucleated lymph node tissues were fixed in formalin so as to be subjected to pathological inspection.

The results are shown in Table 2.

TABLE 2

| Group | Dosage | Region to which the medicine was administered | Interval for administration | Diameter of tumor |
| --- | --- | --- | --- | --- |
| Controlled group | — | Subcutis of a femoral region | 3 times/week | 71.2 ± 35.9 |
| HA-MMC | 0.1 mg/kg | Subcutis of a femoral region | 3 times/week | 22.9 ± 5.3 |
| HA-MMC | 1.0 mg/kg | Subcutis of a femoral region | 3 times/week | 32.0 ± 14.6 |
| MMC | 0.1 mg/kg | Subcutis of a femoral region | 3 times/week | 23.8 ± 8.4 |
| MMC | 1.0 mg/kg | Subcutis of a femoral region | 3 times/week | All cases died |

The hypertropy of a lymph node is caused both by cancer metastasis and by the administration of hyaluronic acid in the single form. However, from the fact the size of the lymph node of mouse in the group to which 0.1 mg/kg of the compound of hyaluronic acid and mitomycin C had been administered was approximately the same as that of a mouse in the group to which 0.1 mg/kg of mitomycin C had been singly administered, the compound of the present invention proved to have a stronger metastasis suppressing effect. In the group to which 1 mg/kg of the compound of hyaluronic acid and mitomycin C had been administered, a strong metastasis suppressing effect as well as the weakened side effects was observed. In the pathological inspection, the necrosis of cancer cells was observed in a broader region in the group which the compound had been administered than in the group to which mitomycin C had been singly administered. In this respect, a strong metastasis suppressing effect was also confirmed.

Tumor Growth Suppressing Test (1)

The MethA tumor growth suppressing effect of a compound of hyaluronic acid and mitomycin C will now be explained.

The compound obtained in the Production Example 2 was dissolved in a physiological saline solution for injectants to a concentration of 4% (w/v). The tumor growth suppressing effect of the administration of the compound was compared with that of the administration of mitomycin C in the single form while administering the physiological saline solution to a controlled group.

1×10⁶ of MethA tumor cells were transplanted on the subcutis of the back portion of a female C3H/He mouse. Each group consisted of 5 mice. Each of the compound and mitomycin C was intraperitoneally administered to each mouse in two levels of 0.1 and 1 mg/kg as calculated in terms of mitomycin C. On the day after the transplantation of the cancer cells, the corresponding medicine was administered for the first time and thereafter it was administered three times a week. Each mouse having the cancer cells was slaughtered 21 days after the transplantation, and the minor diameter (nm) and the major diameter (mm) of the cancer tissue was measured. The tumor diameter was expressed by the average of the minor diameter and the major diameter [(minor diameter +major diameter)/2].The weigh of each mouse was also measured 14 days and 21 days, respectively, after the administration.

The results are shown in Table 3.

TABLE 3

| Group | Dosage | Region to which the medicine was administered | Interval for administration | Diameter of tumor |
|---|---|---|---|---|
| Controlled group | — | Abdomen cavity | 3 times/week | 21.2 ± 0.8 |
| HA-MMC | 0.1 mg/kg | Abdominal cavity | 3 times/week | 17.4 ± 5.1 |
| HA-MMC | 1.0 mg/kg | Abdominal cavity | 3 times/week | 19.9 ± 4.7 |
| MMC | 0.1 mg/kg | Abdominal cavity | 3 times/week | 19.9 ± 6.6 |
| MMC | 1.0 mg/kg | Abdominal cavity | 3 times/week | 25.7 ± 1.0 |

The tumor had a low sensitivity to mitomycin C and the tumor of a mouse in the group to which 1 mg/kg of mitomycin was administered was larger than that of a mouse in the controlled group. However, the compound of hyaluronic acid and mitomycin C produced a stronger antitumor effect than mitomycin in the single form in spite of the low sensitivity of the tumor.

Figure 10:
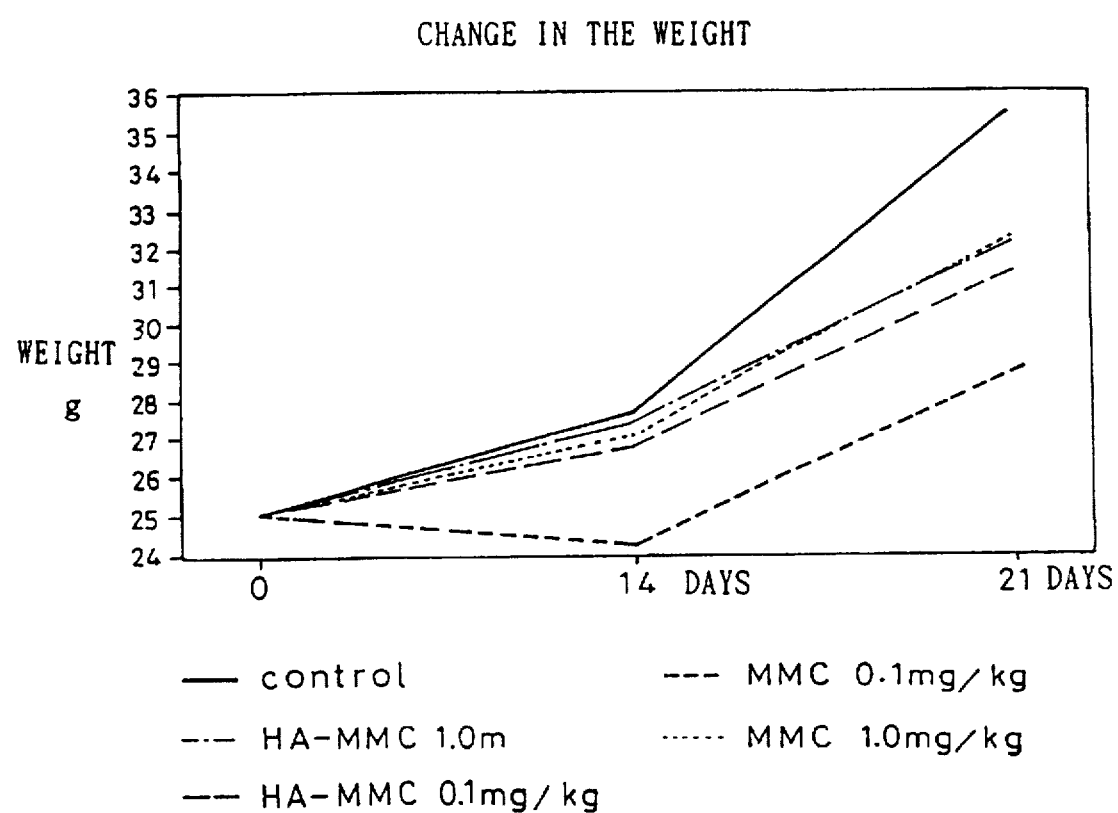
FIG. 10 is an explanatory view of a change in the weight of the mice to which a compound of hyaluronic acid and mitomycin C was administered as compared with those of controlled mice and the mice to which mitomycin C was singly administered.

FIG. 10 shows a change in the weight of the mice during the testing period.

In the group to which 0.1 mg/kg of mitomycin C had been singly administered, the reduction in the weight was observed, but it was not observed in the group to which 0.1 mg/kg of the compound of hyaluronic acid and mitomycin C had been administered. In other words, the harmful side effects of mitomycin C were weakened.

Tumor Growth Suppressing Test (2)

The MH-134 tumor growth suppressing effect of a compound of hyaluronic acid and mitomycin C will now be explained.

The compound obtained in the Production Example 2 was dissolved in a physiological saline solution for injectants to a concentration of 4% (w/v). The tumor growth suppressing suppressing effect of the administration of the compound was compared with that of the administration of mitomycin C in the single form while administering the physiological saline solution to a controlled group.

1×10⁶ of MH-134 ascites hepatoma cells were transplanted on the subcutis of the back portion of a female C3H/He mouse. Each group consisted of 6 mice. Each of mitomycin C and the compound of hyaluronic acid and mitomycin C was intraperitoneally administered to each rat. The dose was 5 mg/kg as calculated in terms of mitomycin C. On the day after the transplantation of the cancer cells, the corresponding medicine was administered for the first times and thereafter it was administered three times a week. Each mouse having the cancer cells was killed 21 days after the transplantation, and the minor diameter (nm) and the major diameter (mm) of the cancer tissue was measured. The tumor diameter was expressed by the product of the minor diameter (mm) and the major diameter (mm). The enucleated lymph node tissues were fixed in formalin so as to be subjected to pathological inspection.

The results are shown in Table 4.

TABLE 4

| Group | Dosage | Region to which the medicine was administered | Interval for administration | Diameter of tumor |
|---|---|---|---|---|
| controlled group | — | Abdomen cavity | 3 times/weeks | 461 ± 227 |
| HA-MMC | 0.5 mg/kg | Abdomen cavity | 3 times/weeks | 81 ± 84 |
| MMC | 0.5 mg/kg | Abdomen cavity | 3 times/weeks | 196 ± 100 |

The results shows that mitomycin C combined with hyaluronic acid suppressed the growth of the tumors to a greater extent than mitomycin C in the single form. That is, administration of the compound of hyaluronic acid and mitomycin C is preferable as a cancer targeting therapy.

EXAMPLE 2

Compound of Hyaluronic Acid and Daunomycin
Production Example 1

While hyaluronic acid is water-soluble and difficult to dissolve in an organic solvent, as described above, many medicinal ingredients such as daunomycin is easy to dissolve in an organic solvent and difficult to dissolve in water.

In order to efficiently combine such medicinal ingredients which are difficult to dissolve in water with hyaluronic acid by amide bonding, the present inventors adopted the following production method.

1 ml of pyridine, 5 ml of 2N hydrochloric acid and 15 ml of dimethylformamide were added to 25 ml of an aqueous solution of 1% sodium hyaluronate. After the mixture was thoroughly stirred, 0.6 g of N-hydroxysuccinimide and 1 g of EDC were added thereto, and the resultant mixture was reacted for 5 fours at room temperature, thereby activating the carboxyl group of the hyaluronic acid.

Thereafter, 5M dipottasium phosphate was added dropwise to the reaction product to adjust the pH to 7.4 and decompose the surplus EDC. 20 mg of ε-aminocaproic acid was then added to the reaction product to react the mixture for 2 hours at room temperature, and the carboxyl group were introduced to the hyaluronic acid through 5 methylene groups. 5N NaOH was added thereto adjust the pH to 12, thereby removing the unstable bonds. Acetic acid was thereafter added to neutralize the acetic acid.

100 ml of ethanol was gently added to the resultant mixture under stirring to precipitate the hyaluronic acid (ethanol precipitation). This operation was repeated twice so as to remove all the low-molecular substances.

100 mg of the hyaluronic acid with the spacer introduced thereinto was dissolved in 9 ml of distilled water. 1 ml of pyridine, 5 ml of 2N hydrochloric acid and 4ml of dimethylformamide were added to the solution and uniformly mixed. After 20 mg of daunomycin was added to the thus-obtained uniform solution, 100 mg of EDC was gradually added to start reaction. 5 hours after the addition of EDC, 2 ml of a 1M sodium acetate buffer solution was added and the mixture was stirred for 30 minutes, thereby decomposing the surplus EDC.

30 ml of acetone was gradually added dropwise to the reaction product under stirring so as to precipitate the hyaluronic acid. The precipitate was gathered by centrifugation. By repeating this acetone precipitating process three times, a pure compound of hyaluronic acid and daunomycin was obtained. The final precipitate was dried at room temperature by a vacuum drier to obtain an orange powder.

Figure 11:
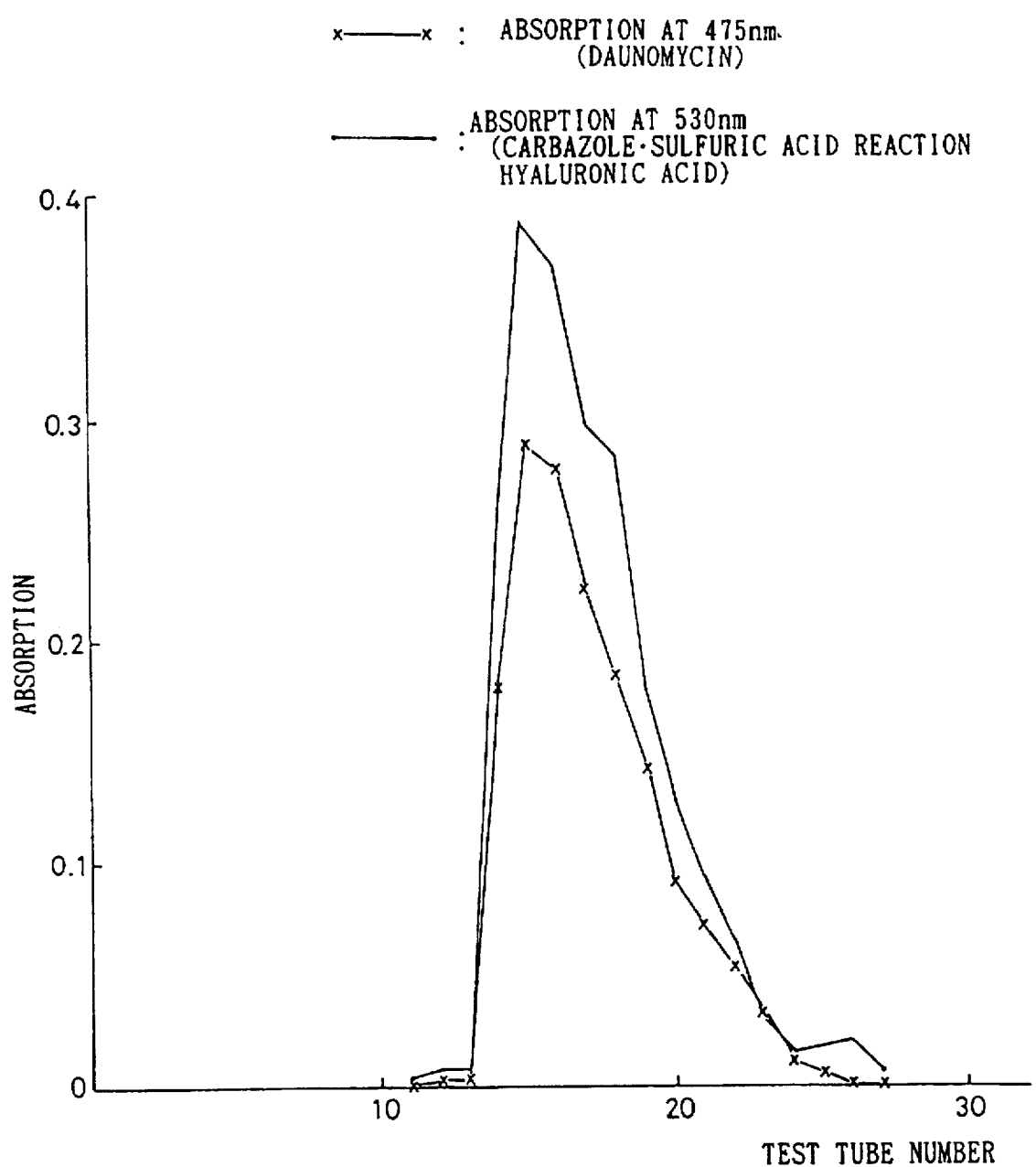
FIG. 11 is an explanatory view of the gel permeation pattern of a compound of hyaluronic acid and daunomycin according to the present invention.

The powder obtained was dissolved in an isotonic phosphoric acid buffer solution to a concentration of 0.5% (w/v) and filtered out through a membrane filter of 0.22 µ to obtain an axenic injectant. When the solution was diluted to 5 times by the isotonic phosphoric acid buffer solution, added to a gel filtration column of Sephacryl S-200 and detected by the carbazole.sulfuric acid reaction and the absorption of the visible portion, the absorption of the visible derived from daunomycin was detected at 475 nm, which agreed with the eluation position of hyaluronic acid (see FIG. 11).

The compound of hyaluronic acid and daunomycin obtained has the following nature.

(1) Molecular weight: 10 to 10,000 kd (calculated by Sephacryl S-1000 chromatography calibrated by hyaluronic acid having various molecular weights or an intrinsic viscosity method)

(2) Content of anticancer agent (daunomycin): 0.1 to 30 wt % (this ratio can be varied by varying the amount of carbodiimide or N-hydroxysuccinimide as a carboxyl group activator, the amount of ε-aminocaproic acid as a spacer, the amount of anticancer used for the reaction and the reaction time)

(3) Nature: Light orange to dark orange color in an aqueous solution of 0.5% (w/v) of the compound odorless.

(4) Solubility: Soluble to water, physiological saline solution and an isotonic phosphoric acid buffer solution and insoluble to methanol, ethanol, acetone, ether and chloroform.

(5) Color reaction: Positive to carbazole.sulfuric acid reaction, ninhydrine reaction, Elson-Morgan reaction after hydrolysis with acid.

Figure 12:
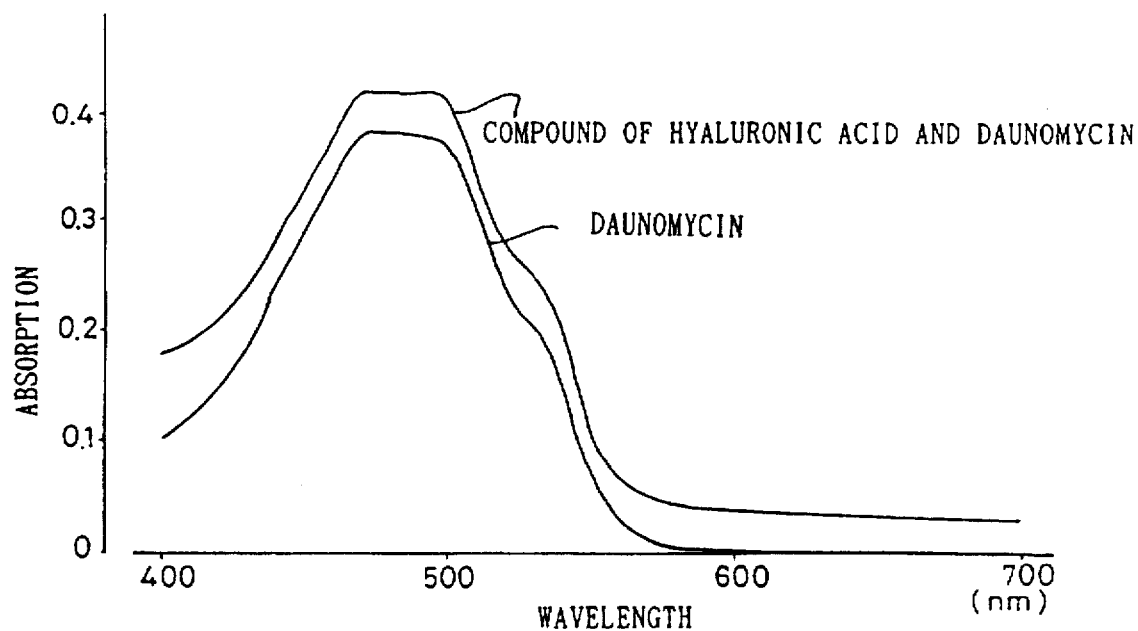
FIG. 12 is an explanatory view of the visible portion absorption spectra of daunomycin and a compound of hyaluronic acid and daunomycin according to the present invention.
Figure 13:
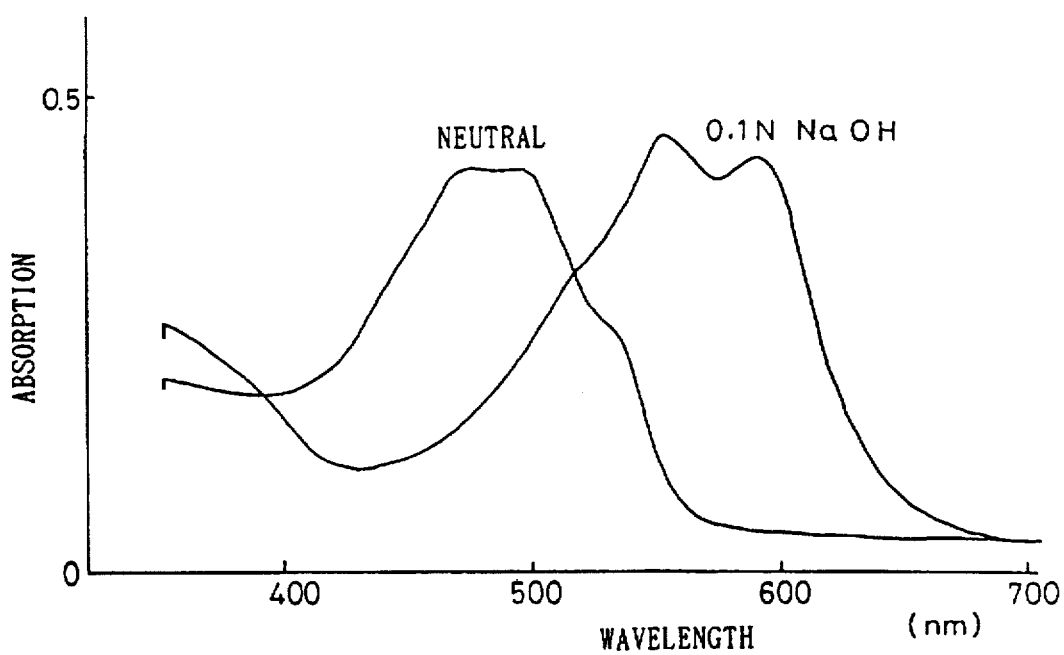
FIG. 13 is an explanatory view of the visible portion absorption spectra of a neutral solution and a 0.1N NaOH solution of a compound of hyaluronic acid and daunomycin.
Figure 14:
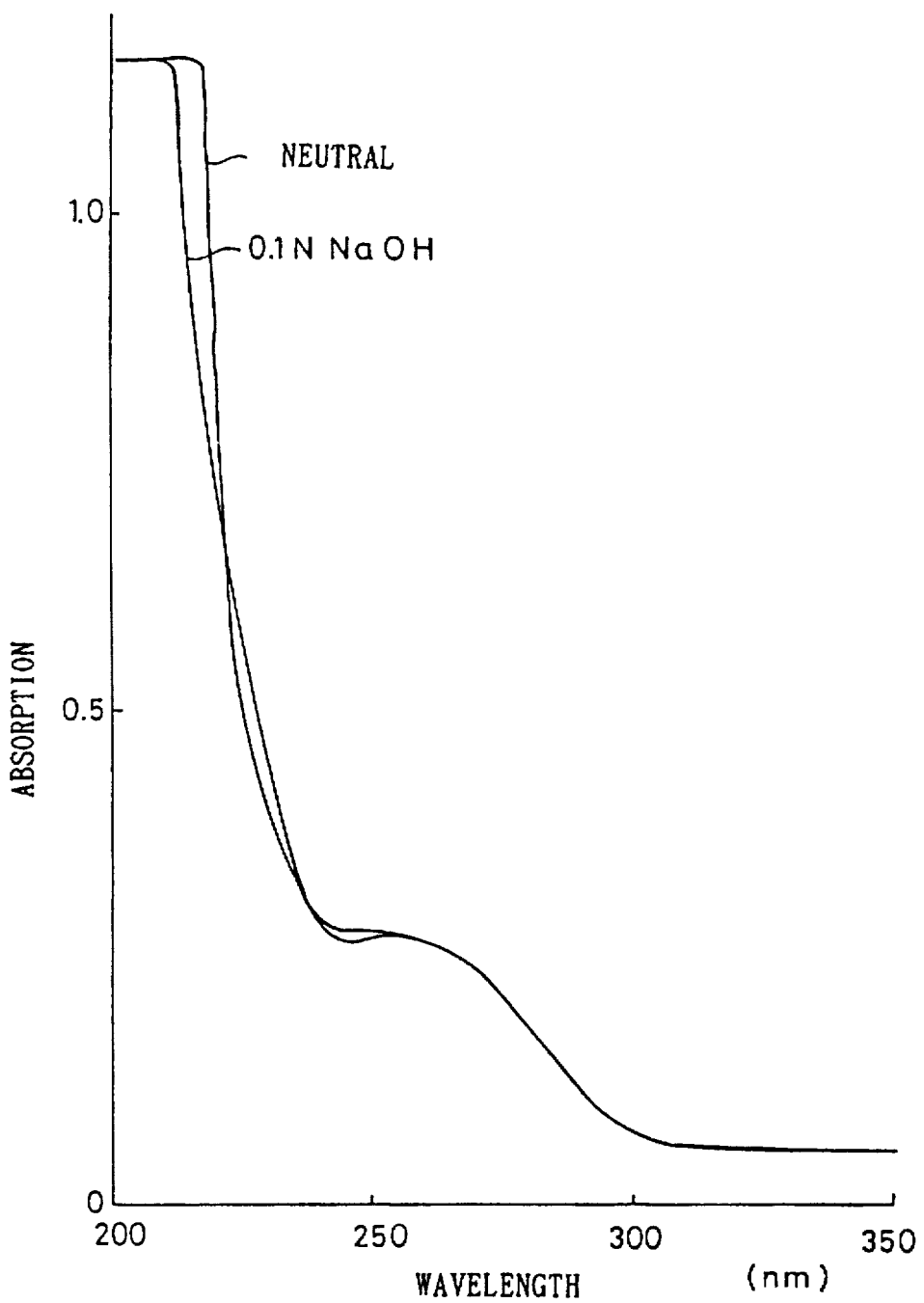
FIG. 14 is an explanatory view of the ultraviolet portion absorption spectra of a neutral solution and a 0.1N NaOH solution of a compound of hyaluronic acid and daunomycin.

(6) Absorption spectrum: The visible portions are absorbed peaks gently at 470 to 500 nm, which agrees with the spectrum of released daunomycin. Under an alkali condition, the absorption of the visible portions shifts to 550 nm and 590 nm. This is due to the existence of the phenolic hydroxyl groups in daunomycin. The ultraviolet portion absorption shows the peak at 255 nm (see FIGS. 12, 13 and 14).

(7) Gel permeation pattern: When the compound is added to a gel permeation column of Sephacryl S-200 and thereafter subjected to a carbazole.sulfuric acid reaction, the peak of the compound is observed at test tube No.15. When the compound is detected at 475 nm, the visible portion (orange) absorption derived from daunomycin is observed (see FIG. 11).

Production Example 2

In order to make hyaluronic acid soluble to an organic solvent, the present inventors experimented on the combination of acetylated hyaluronic acid with a medicinal ingredient in an organic solvent.

500 mg of acetylated hyaluronic acid was dissolved in 100 ml of thoroughly dehydrated dimethylformamide under stirring (0.5% ,w/v). The solution was cooled to −8° to −10° C.

1 ml of isobutyl chloroformate and triethylamine were added to the solution under stirring and reacted at −8° to −10° C. for 90 minutes so as to activate the carboxyl group of the acetylated hyaluronic acid.

Separately from this, 300 mg of daunomycin wad dissolved in a mixture of 10 ml of dimethylformamide and 1 ml of triethylamine and the solution was cooled with ice. The solution was then added to the solution of acetylated hyaluronic acid so as to react the solution under stirring at 0° C. for one night.

The reaction solution was then mixed with ice-cooled 150 ml of purified water to stop the reaction. 5N NaOH was added to the mixed solution so that the pH was 12.5, and the mixture was stirred for 2 hours at room temperature to remove the acetyl group. Thereafter, 5M acetic acid was added to the solution to neutralize it.

Triple the amount of acetone with respect to the whole amount of mixed solution was added to precipitate the thus-synthesized compound of hyaluronic acid and daunomycin. The precipitate was gathered by centrifugation of the solution.

The precipitate was dissolved in 50 ml of a 100 mM sodium acetate buffer solution (pH:6.0). Triple the amount of acetone with respect to the whole amount of solution was added and the preciptate was gathered by the centrifugation of the solution. By repeating this acetone precipitating process three times, a pure compound of hyaluronic acid and daunomycin was obtained. The final precipitate was dried at room temperature by a vacuum drier to obtain an orange powder.

It is possible to produce an axenic injectant from the powder obtained by the same treatment as in the Production Example 1.

The daunomycin content (wt %) calculated from the absorbances of released daunomycin and the compound at 475 nm was 29.6%, and the molecular weight of the compound obtained by an intrinsic viscosity method was 51.7 kd.

Isobutyl chloroformate was used for the reaction in a nonaqueous solution in this example, but N,N-bis[2-oxo-3-oxazolidinyl]phosphorodiamidic chloride, etc. are also usable as a condensation agent.

In these production examples, a synthetic reaction of hyaluronic acid, which is difficult to dissolve in an orangic solvent, and a medicinal ingredient which is difficult to dissolve in water, was enabled for the first time by carrying out the combining reaction in a nonaqueous solution by using acetylated hyaluronic acid, which is soluble to an organic solvent.

EXAMPLE 3

Compound of Hyaluronic Acid and 5FU

Production Example 1

Figure 15:
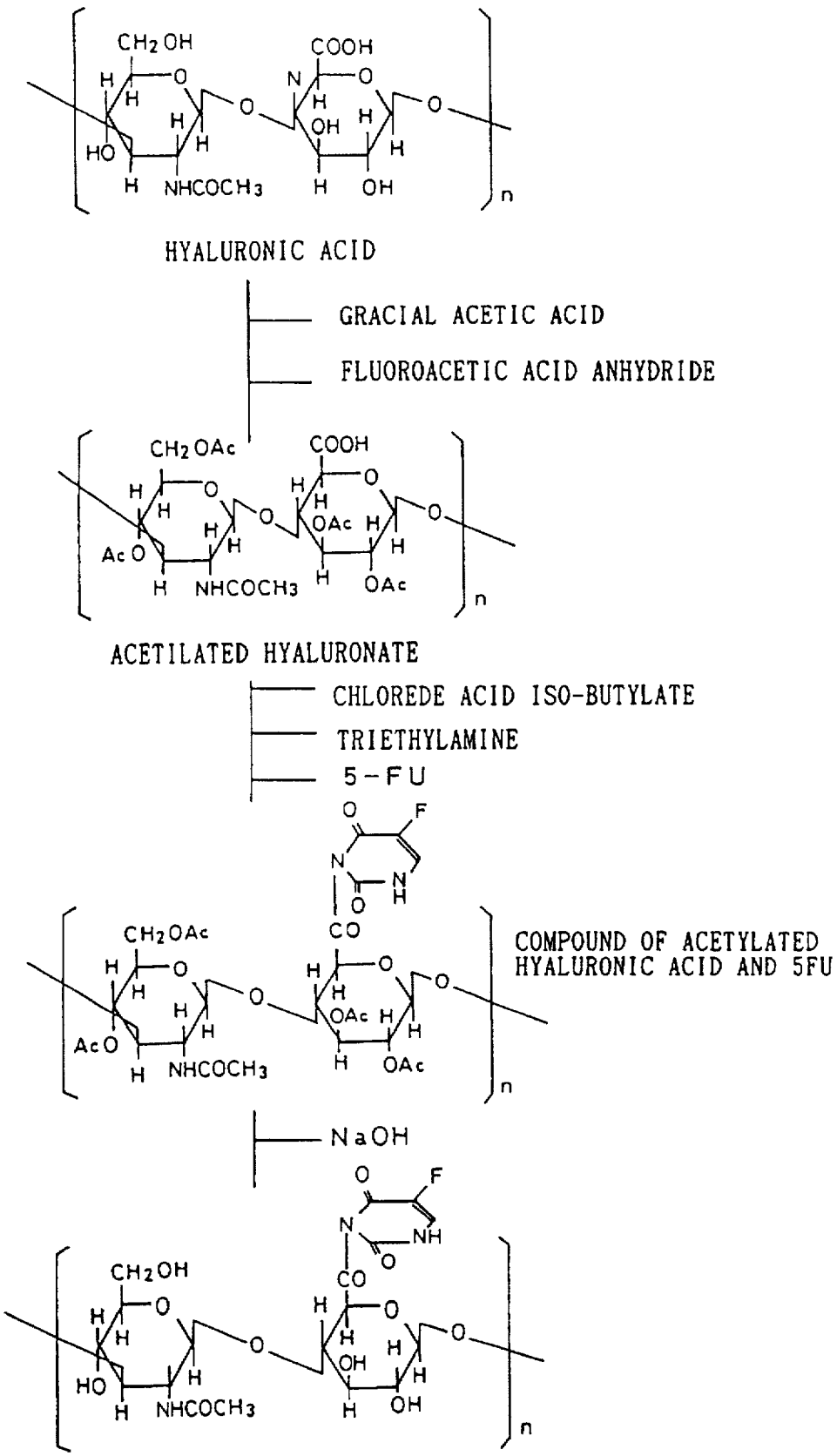
FIG. 15 is an explanatory view of a process for preparing a compound of hyaluronic acid and 5FU.

A compound of hyaluronic acid and 5FU was prepared in the method shown in FIG. 15.

500 mg of acetylated hyaluronate and 250 mg of 5-fluorouracyl (5FU) was dissolved in 50 ml of pyridine.

Separately from this, 0.55 ml of 2-chloropyridine was added to 0.9 ml of methyl p-toluenesulfonic acid and the mixture was stirred for 30 minutes to prepare a pyridinium salt. The pyridine solution of hyaluronic acid and 5FU was gradually added dropwise to the pyridinium salt solution under stirring. When the mixed solution became uniform, the temperature was raised to 50° C. to react the mixed solution for 36 hours.

After the end of the reaction, the reaction product was cooled with ice and five times the amount of n-hexane with respect to the amount of the reaction product was added thereto to precipitate the synthesized compound of acetylated hyaluronic acid and 5FU. The preciptate was gathered by the centrifugation of the solution at 0° C. Half amount of the precipitate was dissolved in 25 ml of dimethylformamide and five times the amount of purified water with respect to the whole amount of solution was added to precipitate the target compound.

By repeating this water precipitating process three times, a pure compound of acetylated hyaluronic acid and 5FU was obtained. The final precipitate was dried at room temperature by a vacuum drier to obtain 148 mg of a while powder.

Figure 16:
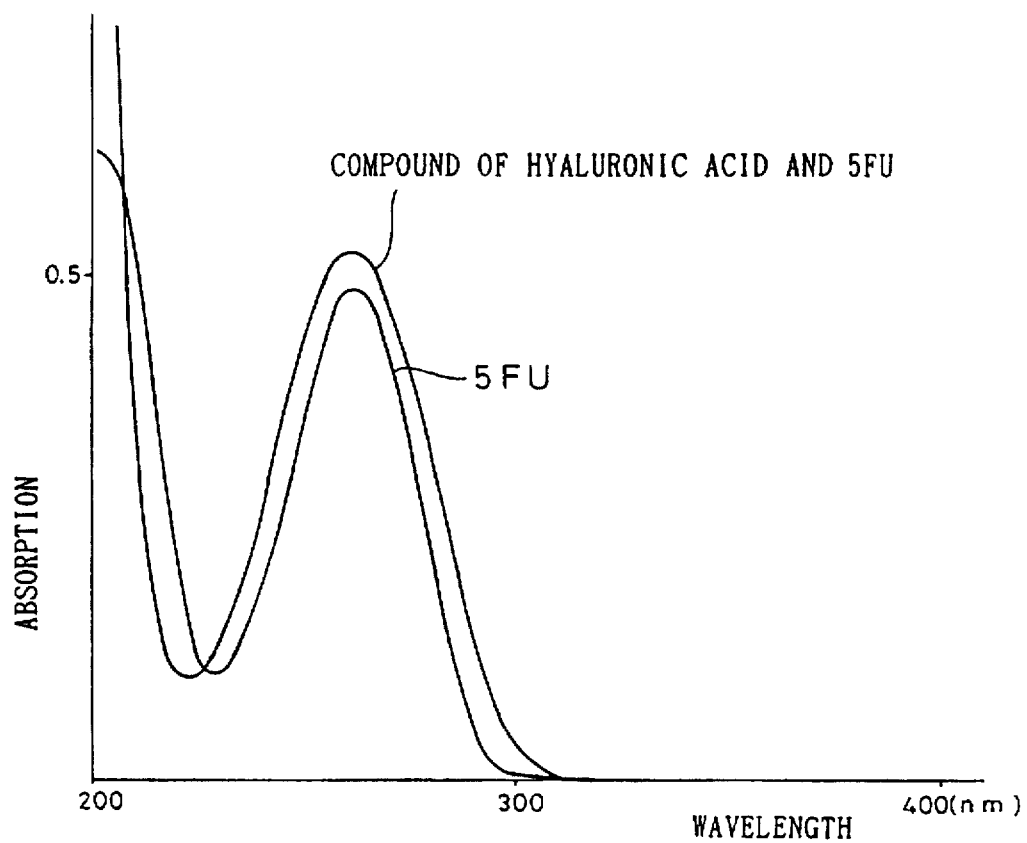
FIG. 16 is an explanatory view of the ultraviolet portion absorption spectrum of a compound of hyaluronic acid and 5FU.
Figure 17:
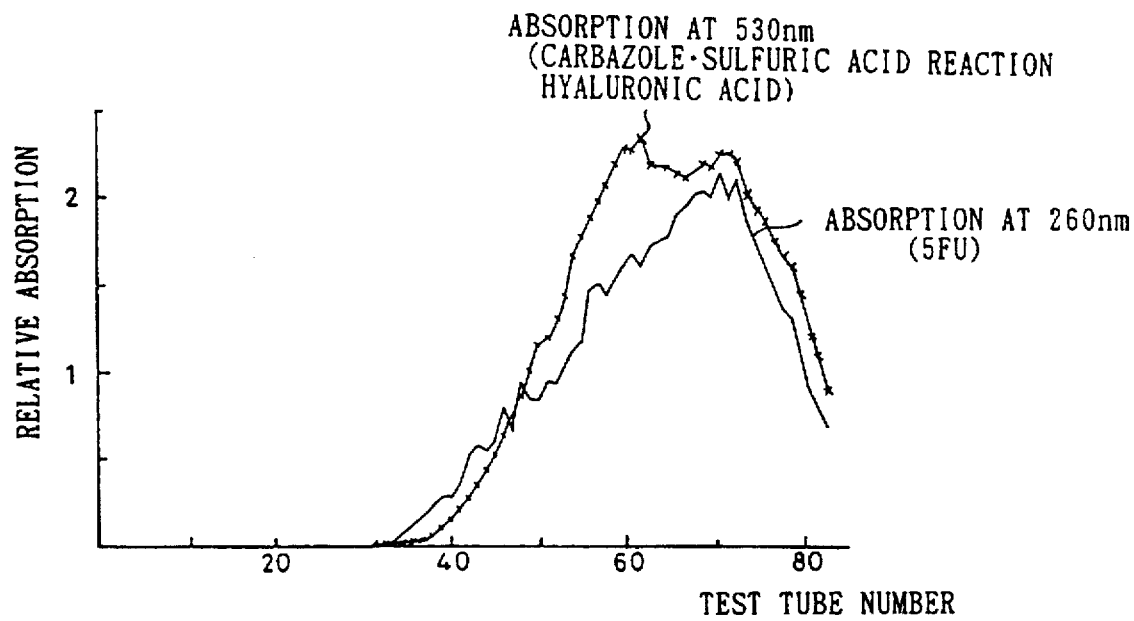
FIG. 17 is an explanatory view of the gel filtration pattern of a compound of hyaluronic acid and 5FU.

When the 5FU content was calculated after removing the acetyl groups from the compound for the purpose of accurate calculation, it was 2.0%. Part of the precipitate was dissolved in ethanol to measure the ultraviolet portion absorption, the absorption of the ultraviolet portion derived from 5FU was observed at 260 nm (see FIG. 16). When the elution patterns of hyaluronic acid (at 530 nm) and 5FU (at 260 nm) were compared, both approximately agreed with each other (see FIG. 17), which suggested that a compound of hyaluronic acid and 5FU had been produced.

The molecular weight of the compound of acetylated hyaluronic acid and 5FU calculated by adding the molecular weight of the acetyl residues to the molecular weight of the compound of hyaluronic acid and 5FU which was obtained in the Production Example 1 was about 170 kd.

The compound of acetylated hyaluronic acid and 5FU obtained in Production Example 1 is oil-soluble. If the compound is dissolved in a small amount of organic solvent such as ethanol, and a physiological saline solution is added to the solution of the compound, the mixed solution takes the form of a gel. When the gel is buried in the regional lymph nodes of a cancer region, the gel gradually disintegrates and the compound of acetylated hyaluronic acid and 5FU gradually moves to the lymph nodes extending over a long time, so that the compound also has a striking effect on the prevention of cancer metastasis through lymph nodes.

Since it is possible to directly bury the gel in a cancer, the concentration of the anticancer at a cancer region is much higher as compared with any other administration method, so that a considerable cancer regression effect can be expected. If the gel is administered into an artery, the artery at a cancer portion is blocked, thereby functioning as a cancer embolus agent which is easy to administer and is expected to have a high anticancer effect.

Production Example 2

The compound of acetylated hyaluronic acid and 5FU produced in Production Example 1 was suspended in 1N NaOH and the suspension was stirred at room temperature for 2 hours to sever the bond of the acetyl group with the hydroxyl group of hyaluronic acid. After neutralizing the suspension by adding 5N acetic acid, triple the amount of acetone was added thereto to precipitate the synthesized compound of hyaluronic acid and 5FU. The preciptate was gathered by the centrifugation of the suspension.

The precipitate was dissolved in 25 ml of 100 mM sodiumacetate buffer solution (pH: 6.0). Triple the amount of acetone with respect to the solution was added to precipitate a compound of hyaluronic acid and 5FU. The precipitate was gathered by the centrifugation of the solution. By repeating this acetone precipitating process three times, a pure compound of hyaluronic acid and 5FU was obtained. The final precipitate was dried at room temperature by a vacuum drier to obtain a white powder.

The powder obtained was dissolved in an isotonic phosphoric acid buffer solution to a concentration of 0.5% (w/v) and filtered out through a membrane filter of 0.22 μ to obtain an axenic injectant.

In this example, the 5FU content (wt %) calculated from the absorbances of the free 5FU and the compound at 260 nm was 2.3%.

The molecular weight of the compound obtained by an intrinsic viscosity method was 145 kd.

Example 3 is characterized in the fact that acetylated hyaluronic acid is used as a starting material. Since it is possible to bring acetylated hyaluronic acid into reaction in an organic solvent, the preparation of a compound of hyaluronic acid and 5FU has been enabled.

EXAMPLE 4

Compound of Hyaluronic Acid and Epirubicin
Production Example 1.5 g of acetylated hyaluronic acid was dissolved in 100 ml of thoroughly dehydrated dimethylformamide under stirring (1.5% , w/v). The solution was cooled to about −10° C. 750 μ of iso-butyl chloroformate and triethylamine were gently added dropwise to the solution under stirring in that order. The mixture was stirred for further 1 hour to activate the carboxyl group of the acetylated hyaluronic acid.

Separately from this, 250 mg of epirubicin was dissolved in 10 ml of dimethyl formamide. After the dissolution, 750 μl of triethylamine was added and the mixed solution was cooled to 0° C. This solution was gradually added dropwise to the acetylated hyaluronic acid solution. The mixed solution was reacted at 4° C. for one night while the entire part thereof was gently stirred.

Thereafter, 200 ml of purified water which had been cooled with ice was added to the reaction product to stop the reaction. 5N NaOH was added to the mixed solution so that pH was 12 to 13, and the mixture was reacted at 4° C. for 2 hours to remove the acetyl group. Thereafter, 5M acetic acid was added to neutralized the solution. Acetone was then added until a compound of hyaluronic acid and epirubicin was obtained as dark red precipitate. The precipitate was centrifugally washed two times with 0.1M sodium acetate buffer solution to remove the unreacted epirubicin.

The final precipitate was dried under a vacuum by a vacuum drier to obtain a pure compound of hyaluronic acid and epirubicin in the form of a dark red powder.

It is possible to produce an injectant for subcutaneous administration, celiac administration or the like by dissolving part of the powder obtained in a physiological saline solution for injectants.

It is also possible to produce an axenic injectant from the powder by dissolving it in a physiological saline solution for injectants containing 20 to 40% of ethanol or propylene glycol and filtering the resultant solution through a membrane filter of 0.22 μ.

The epirubicin content (wt %) calculated from the absorbances of the free epirubicin and the compound at 495 nm was 12.7%, and the molecular weight of the compound obtained from the elution position of gel permeation and a molecular weight calibration curve was 70 kd.

The compound of hyaluronic acid and epirubicin obtained has the following nature.

(1) Molecular weight: 10 to 10,000 kd (2) Content of anticancer agent (epirubicin): 0.1 to 45 wt %

(3) Nature: Light red to dark red in an aqueous solution, hydrous solution or suspension of 0.5% (w/v) of the compound, non-odorous (4) Solubility: Soluble to water, physiological saline solution and isotonic phosphoric acid buffer solution when the epirubicin content is comparatively low, while difficult to dissolve therein when the epirubicin content is high. Soluble to a physiological saline solution containing 20 to 40% ethanol or propylene glycol. Difficult to dissolve in ethanol and acetone. Insoluble to ether and hexane.

(5) Color reaction: Positive to a carbazole.sulfuric acid reaction, and an Elson-Morgan reaction after hydrolysis with acid.

Figure 18:
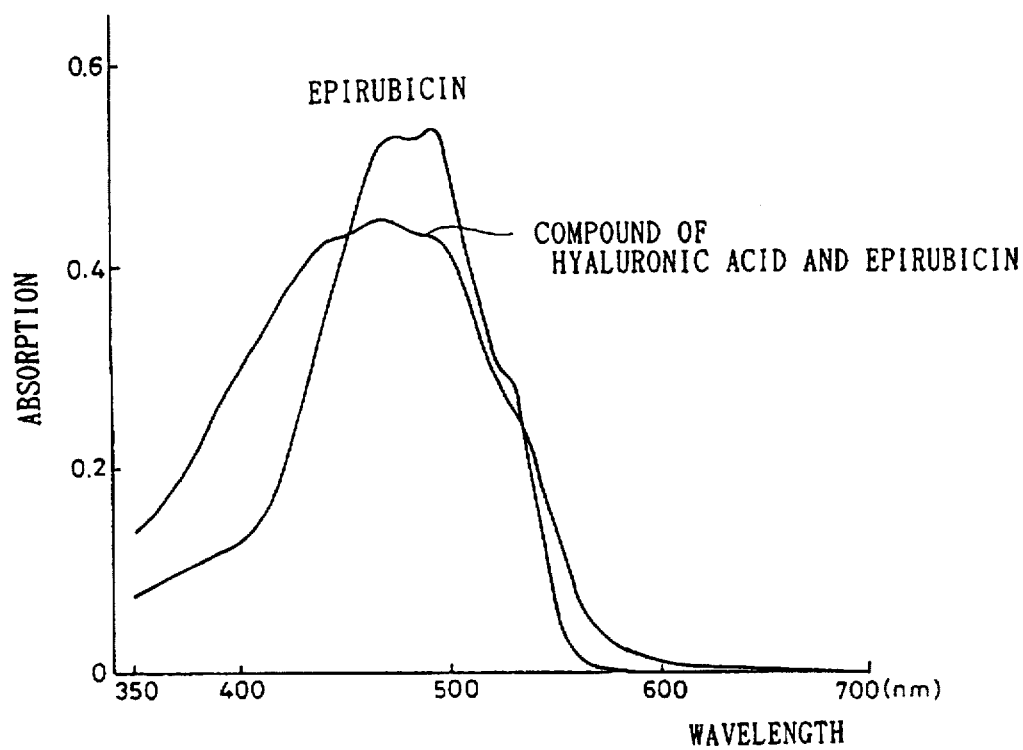
FIG. 18 is an explanatory view of the visible portion absorption spectrum of a compound of hyaluronic acid and epirubicin.

(6) Visible portion absorption: Broad peaks are observed at 470 to 480 nm, and the shoulder thereof is in the vicinities of 450 nm and 490 nm (see FIG. 18).

(7) Release of anticancer agent:epirubicin is released in the living body with the decomposition by metabolism of hyaluronic acid.

(8) Gel permeation pattern: When the compound is added to a gel permeation column of Sephacryl S-300 and thereafter subjected to a carbazole.sulfuric acid reaction, the peak of the compound is observed at the position of a molecular weight of about 70 kd. At the same position, the ultraviolet portion absorption derived from epirubicin is observed (see FIG. 19).

Entosomatic Kinetics Test

The entosomatic kinetics test applied to a compound of hyaluronic acid and epirubicin will be explained in the following.

The compound of hyaluronic acid and epirubicin prepared in Production Example was suspended to a physiological saline solution to a concentration of 1% (w/v).

The solution was administered to male SD rats each having a weight of 400 to 500 g. Each group consisted of 5 rats. 100 µl of the liquid medicine (equivalent to 1 mg of the compound) was administered to the subcutis of a femoral region of each rat. 24 hours after the administration, blood was drawn from the heart of each rat under etherization until it died. Immediately thereafter the liver, the mesenteric lymph nodes, the iliac lymph nodes and the inguinal lymph nodes were enucleated to measure the wet weigh of each tissue.

10 mM phosphoric acid buffer solution of 1.15% of KCl (pH: 7.8) were added to each of the enucleated tissues to produce a homogenate. The plasma, and each homogenate with protease (pronase) added thereto so that final concentration was 0.2% were allowed to stand at 37° C. for one night so as to digest the corresponding protein. Thereafter, cetylpyridinium chloride was added to each tissue so that the final concentration was 0.2% and the compound of hyaluronic acid and epirubicin was precipitate. The precipitate was extracted with 0.5M Nacl.

The concentration of the compound of hyaluronic acid and epirubicin was measured at an excitation wavelength of 470 nm and a fluorescence wavelength of 585 nm (pH: 4.6).

Figure 20:
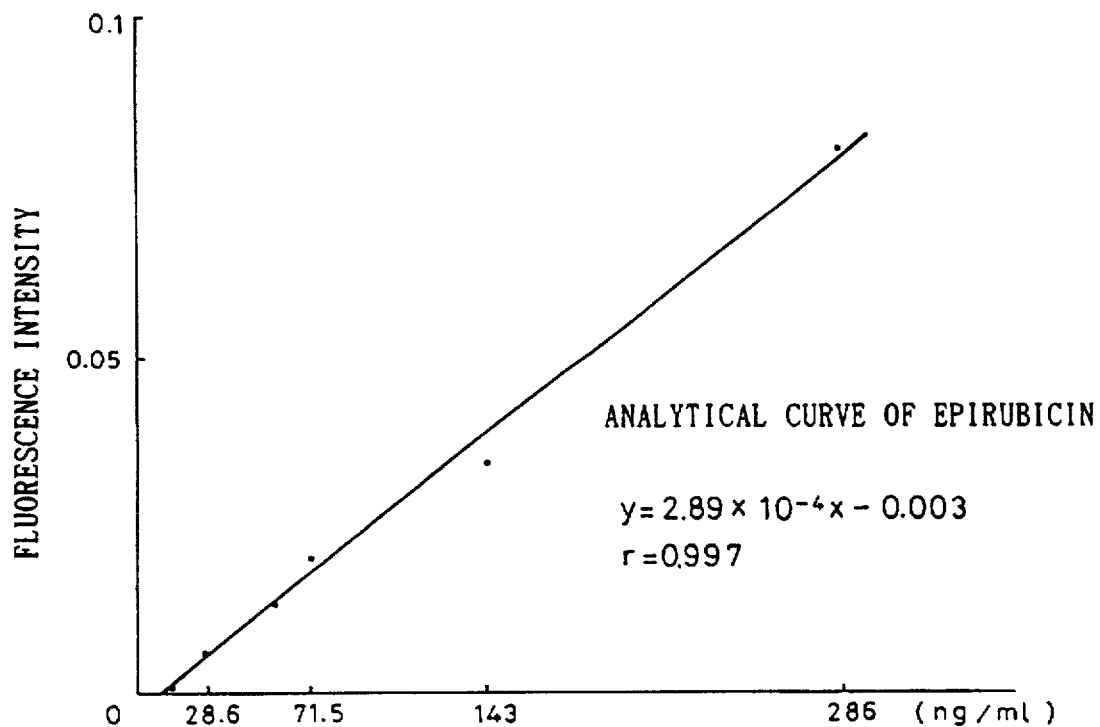
FIG. 20 is an explanatory view of the analytical curve of epirubicin used in Example 4.
Figure 21:
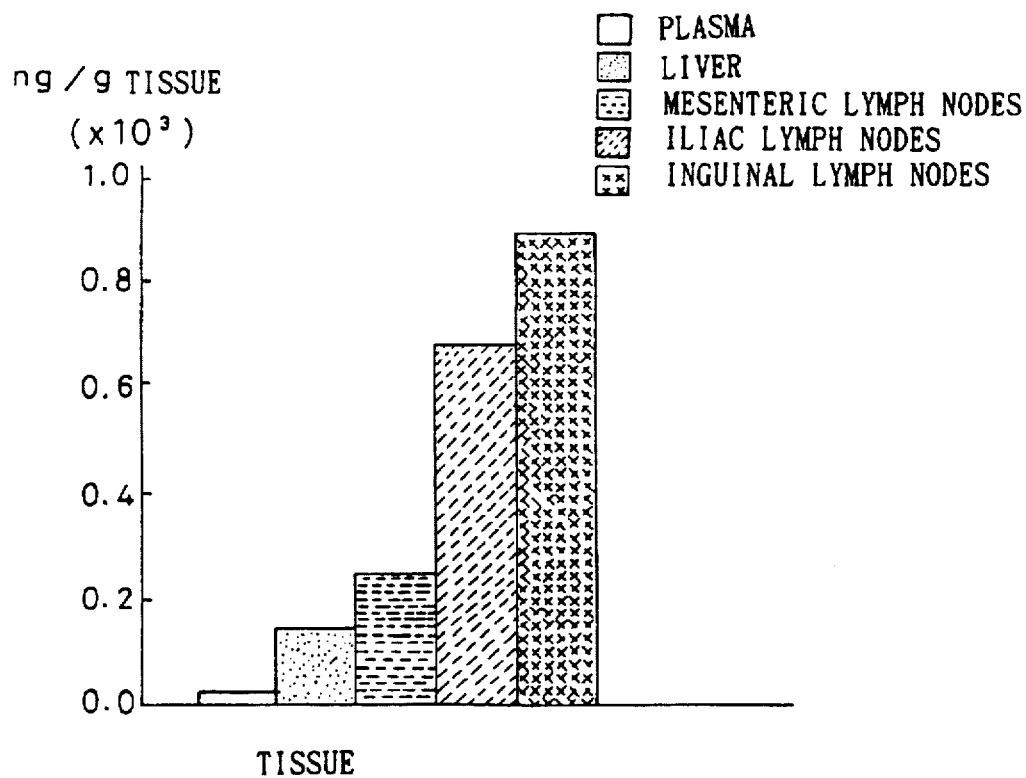
FIG. 21 is an explanatory view of the distribution of a compound of hyaluronic acid and epirubicin in each tissue after 24 hours passed since the administration of the compound of hyaluronic acid and epirubicin to the subcutis of a femoral region of a rat.

FIG. 20 shows the analytical curve of epirubicin. A good linearity was observed in the range of about 10 to 300 ng/ml.

Figure 19:
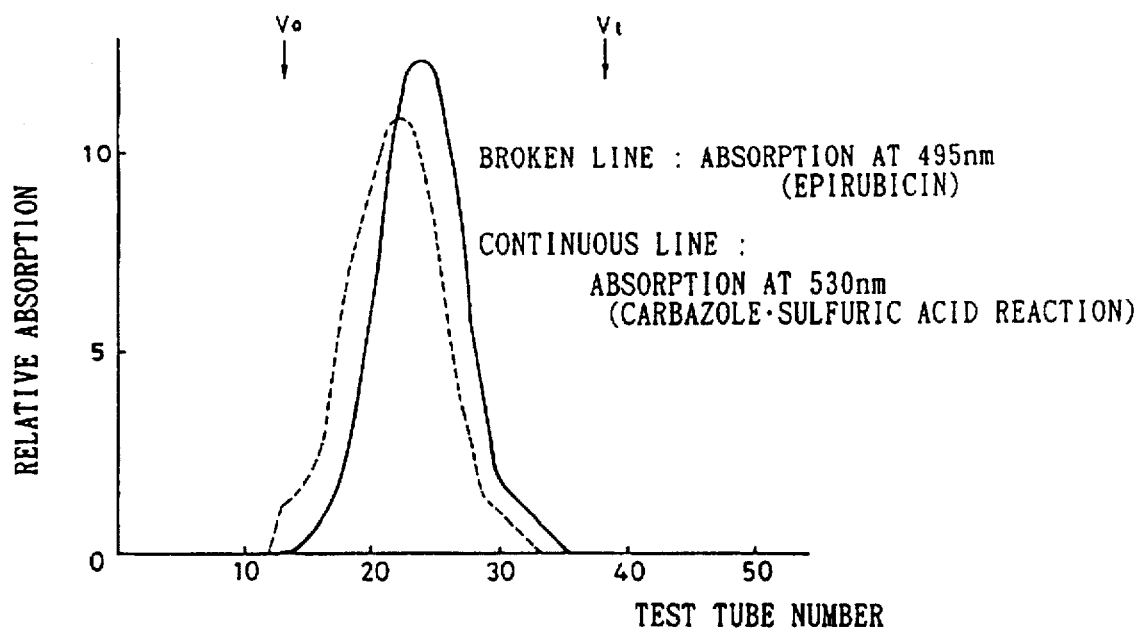
FIG. 19 is an explanatory view of the gel permeation pattern of a compound of hyaluronic acid and epirubicin.

FIG. 19 shows the results of the measurement of the concentration of the compound of hyaluronic acid and epirubicin in plasma, liver, mesenteric lymph nodes, iliac lymph nodes and inguinal lymph nodes.

A very high directivity was observed in the iliac lymph nodes and the inguinal lymph nodes, which were the regional lymph nodes of the femoral region. The concentration of the compound of hyaluronic acid and epirubicin in these lymph nodes were about 35 times and 45 times, respectively, as high as the concentration in the plasma. They were about 5 to 7 times as high as that in the liver, which is known as a hyaluronic acid metabolic tissue.

Although carbon particles (black fluid) move to lymph nodes, since they are not decomposed by metabolism, they are stored in the lymph nodes. In contrast, it was confirmed that the compound of hyaluronic acid and epirubicin (coloring red) was not stored in lymph nodes but metabolized therein.

As described above, it was confirmed that the compound of hyaluronic acid and epirubicin had about 50 times as high a directivity to the iliac lymph nodes and the inguinal lymph nodes, which are the action region, namely, the regional lymph nodes of the femoral region, as the directivity to the plasma.

EXAMPLE 5

Compound of Hyaluronic Acid and Cytocine Arabinoside

Production Example 1

1 g of acetylated hyaluronic acid was dissolved in 100 ml of dehydrated dimethylformamide (1%, w/v). The solution was cooled to about −10° C. 1 ml of isobutyl chloroformate and triethylamine were gently added dropwise to the solution under stirring in that order. The mixture was stirred for further 1 hour to activate the carboxyl groups of the acetylated hyaluronic acid.

Separately from this, 300 mg of cytocine arabinoside was dissolved in 10 ml of dimethyl formamide. After the dissolution, 1 ml of triethylamine was added and the mixed solution was cooled to 0° C. This solution was gradually added dropwise to the acetylated hyaluronic acid solution. The mixed solution was reacted at 0° C. for one night while the entire part thereof was gently stirred.

Thereafter, the reaction product was mixed with 300 ml of purified water to stop the reaction. The precipitated cytocine arabinoside acetylated hyaluronate was separated by centrifugation. By repeating this purified water precipitating process by centrifugation five times, the unreacted cytocine arabinoside was removed.

The final precipitate was dried under a vacuum by a vacuum drier to obtain pure cytocine arabinoside acetylated hyaluronate. The product was a white fibrous substance.

It is possible to produce an axenic injectant from the compound by dissolving it in distilled water for injectants containing 30 to 50% of propylene glycol or ethanol and filtering the resultant solution through a membrane filter of 0.22 µ.

It is also possible to produce an effective cancer embolus remedy agent in the form of a suspending gel by dissolving the compound in a physiological saline solution for injectants containing 10 to 20% of propylene glycol or ethanol.

Production Example 2

The compound of acetylated hyaluronic acid and cytocine arabinoside was further treated with an alkali in the following manner, thereby obtaining a compound of hyaluronic acid and cytocine arabinoside.

500 mg of a compound of acetylated hyaluronic acid and cytocine arabinoside was suspended in 50 ml of purified water. 5N NaOH was added to the suspension under stirring so that the final concentration was 0.1N. The suspension was stirred for 3 hours at room temperature to remove the O-acetyl group and dissolve the precipitate. Thereafter, 5M acetic acid was added to the solution to neutralize it.

Triple the amount of acetone with respect to the whole amount of mixed solution was added to precipitate the compound of hyaluronic acid and cytocine arabinoside produced. The precipitate was gathered by centrifugation of the solution.

The precipitate was dissolved in 50 ml of a 100 mM sodium acetate buffer solution. Triple the amount of acetone with respect to the whole amount of solution was added to precipitate the compound of hyaluronic acid and cytocine arabinoside and the precipitate was gathered by the centrifugation of the solution. By repeating this acetone precipitating process three times, a pure compound of hyaluronic acid and cytocine arabinoside was obtained. The final precipitate was dried at room temperature by a vacuum drier to obtain 415 mg of a white powder.

It is possible to produce an axenic injectant from the powder obtained by the same treatment as in the Production Example 1.

The cytocine arabinoside content (wt %) calculated from the absorbances of the free cytocine arabinoside and the compound at 272 nm was 16.43%, and the molecular weight of the compound obtained by an intrinsic viscosity method was 86.8 kd.

The compound of hyaluronic acid and cytocine arabinoside obtained has the following nature.

(1) Molecular weight: 10 to 10,000 kd
(2) Content of anticancer agent (cytocine arabinoside):0.1 to 45 wt %
(3) Nature: transparent water-white in an aqueous solution, a hydrous solution or suspension of 0.5% (w/v) of the compound, non-odorous
(4) Solubility: Soluble to water, physiological saline solution and isotonic phosphoric acid buffer solution, and insoluble to methanol, acetone, ether and chloroform.

Cytocine arabinoside-acetylated hyaluronate is soluble to an aqueous solution of 30 to 50% of propylene glycol or ethanol and suspends in the form of a gel in an aqueous solution of 10 to 20% of propylene glycol or ethanol. It is soluble to dimethyl formamide, dimethyl sulfoxide, ethylene glycol and propylene glycol and insoluble to water, acetone, ether and hexane.

Figure 22:
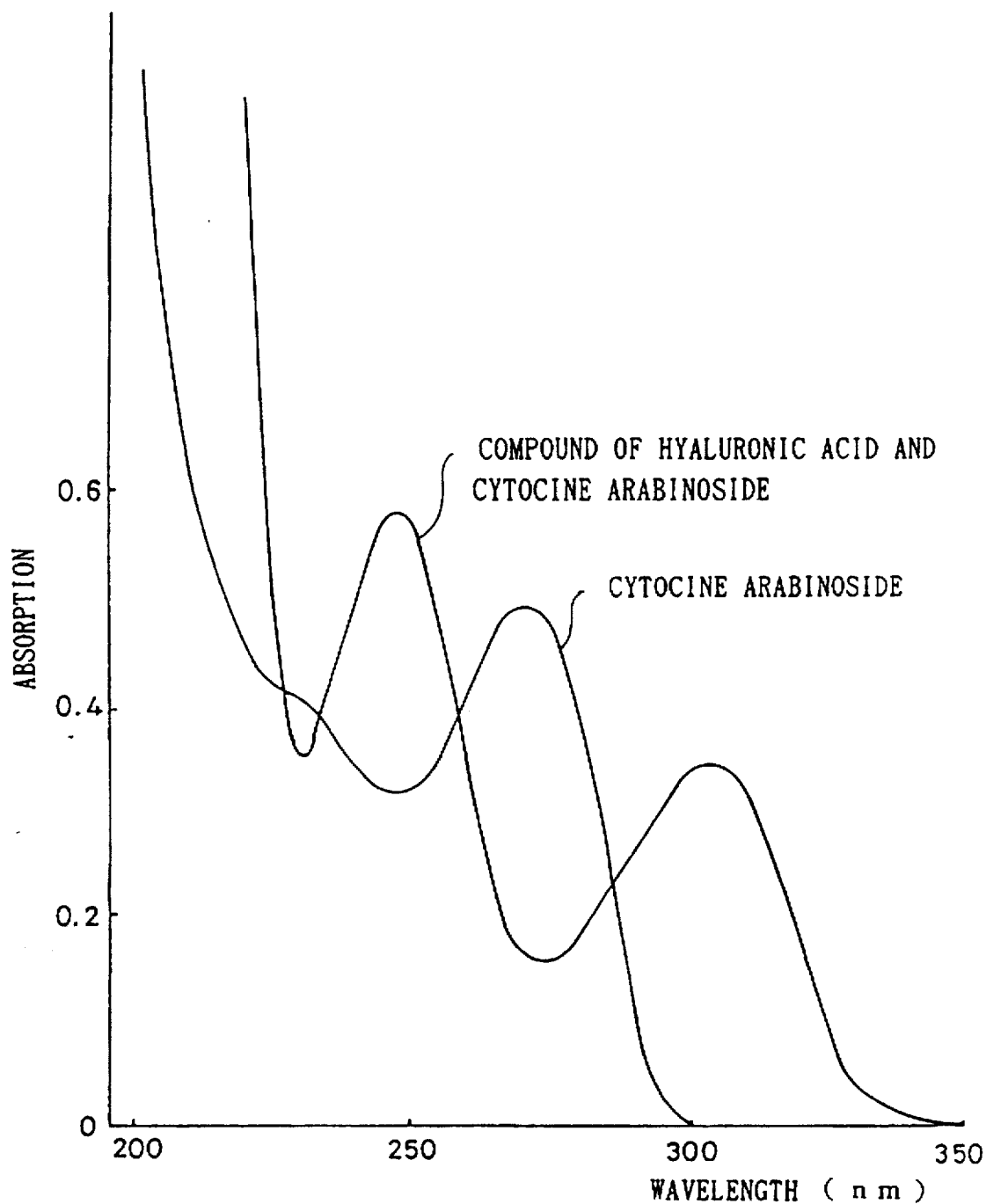
FIG. 22 is an explanatory view of the visible portion absorption spectrum of a compound of hyaluronic acid and cytocine arabinoside.
Figure 23:
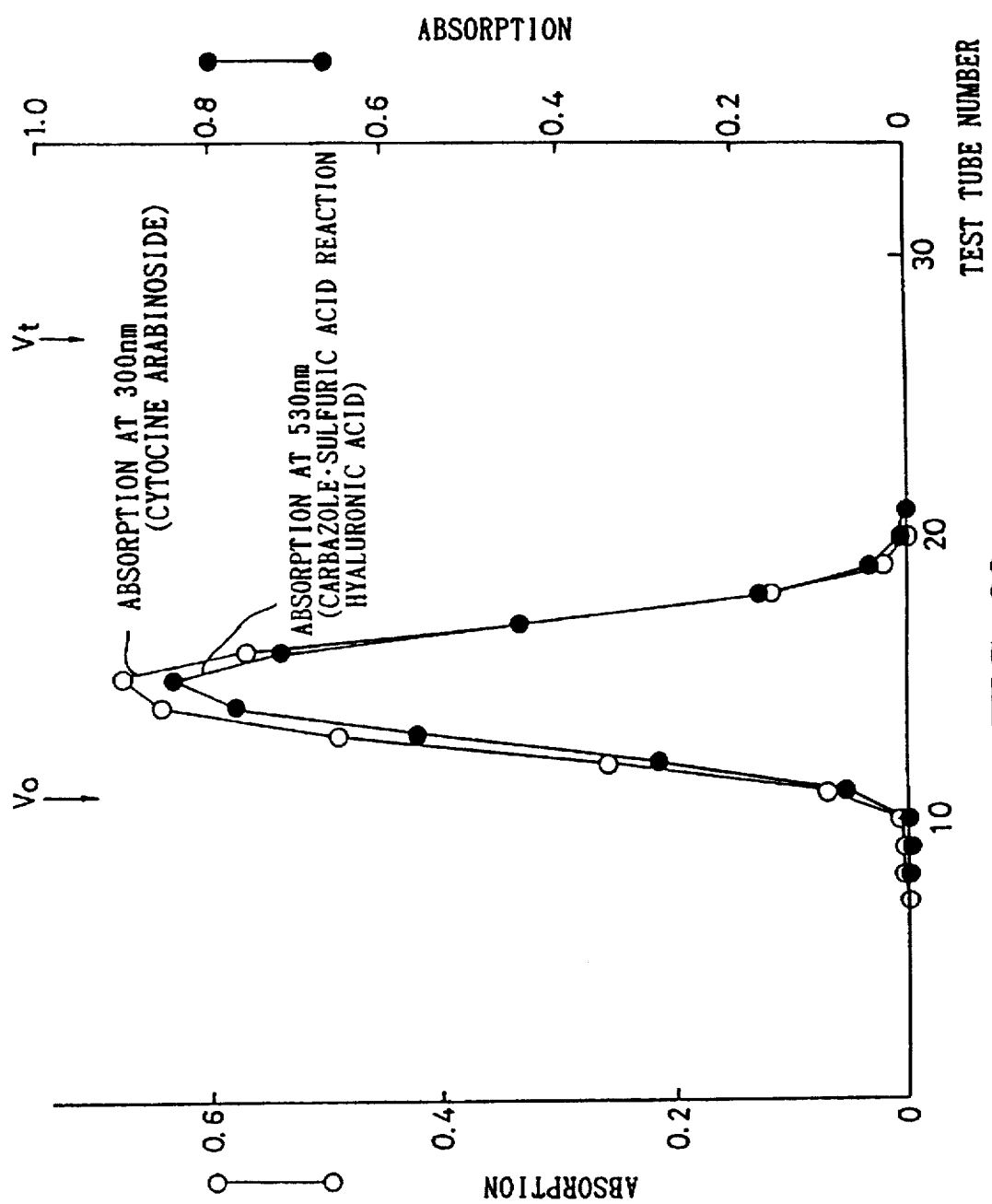
FIG. 23 is an explanatory view of gel filtration pattern of a compound of hyaluronic acid and cytocine arabinoside.

(5) Color reaction: Positive to a carbazole.sulfuric acid reaction, and an Elson-Morgan reaction after hydrolysis with acid.
(6) Ultraviolet portion absorption: The peaks of the spectrum are at 247 nm and 305 nm (see FIG. 22).
(7) Release of anticancer agent: cytocine arabinoside is released with the decomposition of the hyaluronic acid by metabolism in the living body.
(8) Gel permeation pattern: When the compound is added to a gel permeation column of Sephacryl S-200 and thereafter subjected to a carbazole.sulfuric acid reaction, the peak of the compound is observed at the position of a molecular weight of about 90 kd. At the same position, the ultraviolet portion absorption derived from cytocine arabinoside is observed (see FIG. 23).

As described above, a compound of hyaluronic acid and medicinal ingredient of the present invention has a high directivity to a specific tissue and can fully display the medicinal effect while efficiently suppressing harmful side effects to the other tissues.

We claim:

1. A therapeutic agent consisting essentially of an anticancer agent and hyaluronic acid which can be administered to a patient, wherein the improvement comprises a therapeutic agent formed by combining said anticancer agent with a carboxyl group of glucuronic acid residue of hyaluronic acid by amide bonding without a spacer between said anticancer agent and said hyaluronic, said therapeutic agent containing 0.1–45 wt. % of said anticancer agent.

2. A therapeutic agent according to claim 1, wherein the improvement comprises said anticancer agent being a suppressor for cancer metastasis through lymph nodes.

3. A therapeutic agent according to claim 1, wherein the improvement comprises said anticancer agent being non-specific missile medicinal agent for cancer.

4. A therapeutic agent according to claim 2, wherein said hyaluronic acid is acetylated hyaluronic acid and said anticancer agent is a suppressor for a cancer metastasis through a lymph node.

5. A therapeutic agent according to claim 3, wherein said hyaluronic acid is acetylated hyaluronic acid and said anticancer agent is a non-specific missile medicinal agent for cancer.

6. A process for preparing a compound of hyaluronic acid and a water soluble anticancer agent comprising the steps of:
adding pyridine and hydrochloric acid to an aqueous solution of sodium hyaluronate;
stirring the mixture;
adding water soluble carbodiimides as condensing agent and N-Hydroxysuccinimide as an activating agent to said mixture so as to activate said hyaluronic acid;
dissolving the activated hyaluronic acid in a buffer solution; and
adding an aqueous solution of anticancer agent to the resultant solution so as to combine said activated hyaluronic acid with said anticancer agent, thereby forming an amide bond without a spacer between said hyaluronic acid and said anticancer agent.

7. A process for preparing a compound of hyaluronic acid and a water insoluble anticancer agent comprising the steps of:
reacting in an organic solvent having low reactability an acetylated hyaluronic acid with a water insoluble anticancer agent thereby forming an amide bond without a spacer between said hyaluronic acid and said anticancer agent.

8. A process for preparing a compound of hyaluronic acid and a water insoluble anticancer agent accordingly to claim 7 further comprising severing bonds between the acetyl groups and hydroxyl groups of the acetylated hyaluronic acid residue.

9. In a method of treating a patient with an anticancer agent, the improvement comprising administering to said patient a pharmacologically effective amount of the therapeutic agent of claim 1.

10. In a method of treating a patient with an anticancer agent, the improvement comprising administering to said patient a pharmacologically effective amount of the therapeutic agent of claim 9.

11. In a method of treating a patient with an anticancer agent, the improvement comprising administering to said patient a pharmacologically effective amount of the therapeutic agent of claim 3.

12. In a method of treating a patient with an anticancer agent, the improvement comprising administering to said patient a pharmacologically effective amount of the therapeutic agent of claim 4.

13. An injectable composition comprising a pharmacologically effective amount of the therapeutic agent of claim 1 and a pharmaceutically effective carrier thereof.

14. A therapeutic agent according to claim 1, wherein said anticancer agent is mytomycin C which constitutes 0.1–30 wt. % of said therapeutic agent.

15. A therapeutic agent according to claim 14, wherein an aqueous solution of 0.5% (w/v) of said anticancer agent is non-odorous and is light purplish red to dark purplish red.

16. A therapeutic agent according to claim 1, wherein said anticancer agent is daunomycin which constitutes 0.1–30 wt. % of said therapeutic agent.

17. A therapeutic agent according to claim 16, wherein an aqueous solution of 0.5% (w/v) of the therapeutic agent is non-odorous and light orange to dark orange.

18. A therapeutic agent according to claim 1, wherein said anticancer agent is epirubicin which constitutes 0.1–45 wt. % of said therapeutic agent.

19. A therapeutic agent according to claim 18, wherein an aqueous solution, a solution or suspension of 0.5% (w/v) of said therapeutic agent is non-odorous and light red to dark red transparent.

20. A therapeutic agent according to claim 1, wherein said anticancer agent is cytocine arabinoside which constitutes 0.1–45 wt. % of said anticancer agent.

21. A therapeutic agent according to claim 20, wherein an aqueous solution, a hydrous solution or suspension of 0.5% (w/v) of the therapeutic agent is non-odorous and transparent water-white in an aqueous solution.

* * * * *